United States Patent
Kulkarni et al.

(10) Patent No.: US 10,602,923 B2
(45) Date of Patent: *Mar. 31, 2020

(54) FOLDABLE AND PORTABLE OCULAR SYSTEMS

(71) Applicants: Manish Dinkarrao Kulkarni, Pleasanton, CA (US); Manmohan Singh Sidhu, Lathrop, CA (US)

(72) Inventors: Manish Dinkarrao Kulkarni, Pleasanton, CA (US); Manmohan Singh Sidhu, Lathrop, CA (US)

(73) Assignee: Netra Systems, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/112,649

(22) Filed: Aug. 25, 2018

(65) Prior Publication Data

US 2018/0360306 A1 Dec. 20, 2018

Related U.S. Application Data

(63) Continuation of application No. 15/624,689, filed on Jun. 15, 2017, now Pat. No. 10,076,240, which is a continuation-in-part of application No. 14/757,749, filed on Dec. 22, 2015, now Pat. No. 9,717,406, which is a continuation of application No. 13/744,415, filed on Jan. 18, 2013, now Pat. No. 9,247,869.

(60) Provisional application No. 61/587,132, filed on Jan. 17, 2012.

(51) Int. Cl.
| | |
|---|---|
| A61B 3/14 | (2006.01) |
| A61B 3/10 | (2006.01) |
| A61B 3/00 | (2006.01) |
| A61B 34/00 | (2016.01) |

(52) U.S. Cl.
CPC .......... *A61B 3/0083* (2013.01); *A61B 3/0033* (2013.01); *A61B 3/0041* (2013.01); *A61B 3/102* (2013.01); *A61B 34/25* (2016.02); *A61B 2560/0431* (2013.01)

(58) Field of Classification Search
CPC .......... A61B 3/14; A61B 3/0025; A61B 3/12; A61B 3/102; A61B 3/0058
USPC ....................................................... 351/206
See application file for complete search history.

(56) References Cited

U.S. PATENT DOCUMENTS

| | | | |
|---|---|---|---|
| 10,076,240 B2* | 9/2018 | Kulkarni | A61B 3/0041 |
| 2007/0291277 A1* | 12/2007 | Everett | A61B 3/102 |
| | | | 356/497 |
| 2008/0187099 A1* | 8/2008 | Gertner | A61N 5/1017 |
| | | | 378/65 |
| 2017/0127932 A1* | 5/2017 | Walsh | A61B 3/0083 |

* cited by examiner

*Primary Examiner* — Mohammed A Hasan

(57) ABSTRACT

There is a need for robust and portable system, and apparatus for ophthalmology. We propose use of foldable ophthalmic system. Our system will have a chin-rest (or face-rest or forehead rest) that can be folded so that the ocular device could be transported in a brief-case type casing. Our system can be used for many modalities including optical coherence tomography.

18 Claims, 13 Drawing Sheets

FOLDABLE AND PORTABLE OCULAR SYSTEMS

CROSS REFERENCE TO RELATED APPLICATIONS

The instant application is a continuation application and claims priority to the pending U.S. patent application Ser. No. 15/624,689 titled "Foldable Ophthalmic System" filed on Jun. 15, 2017. The entire disclosure of the U.S. patent application Ser. No. 15/624,689 is hereby incorporated by this reference in its entirety for all of its teachings. The application Ser. No. 15/624,689 is a continuation-in-part application and claims priority to the U.S. patent application Ser. No. 14/757,749 (now patented with U.S. Pat. No. 9,717,406) titled "Compact Foldable Apparatus for Ophthalmology" filed on Dec. 22, 2015. The entire disclosure of the U.S. patent application Ser. No. 14/757,749 is hereby incorporated by this reference in its entirety for all of its teachings. The application Ser. No. 14/757,749 is a continuation application and claims priority to the U.S. patent application Ser. No. 13/744,415 (now patented with U.S. Pat. No. 9,247,869) titled "Compact Foldable Apparatus for Ophthalmology" filed on 18 Jan. 2013. The entire disclosure the U.S. patent application Ser. No. 13/744,415 is hereby incorporated by this reference in its entirety for all of its teachings. U.S. patent application Ser. No. 13/744,415 claims priority to provisional U.S. patent application 61/587,132 titled "A Compact Foldable Apparatus for Ophthalmology", filed on 17 Jan. 2012 by the inventors Manmohan Singh Sidhu and Manish D. Kulkarni. This benefit is claimed under 35. U. S. C. $119 and the entire disclosure of the Provisional U.S. patent Application No. 61/587,132 is incorporated here by reference.

FIELD OF TECHNOLOGY

The following description relates to a system, and an apparatus for ophthalmology. The device can be used for diagnosis, evaluation or therapy. The device can be used for ophthalmic imaging and/or diagnosis, anterior segment imaging and/or diagnosis, retinal imaging and/or diagnosis. The apparatus and system can be used for the eyes of the humans as well as the animals.

BACKGROUND

Most of the ophthalmic systems comprise of the chin-rests that are not foldable. A patient, (whose eye needs to be examined), rests his/her chin on this chin-rest so that the eye can be stabilized for useful measurements on the eye. While useful for stabilizing the patient's eye, these chin-rests form a significant part of the device's footprint. Such a chin-rest is a significant hurdle for minimizing the device-form-factor, and building an apparatus or a system that is compact and portable. European patent (publication number EP1441640 A2 and EP1441640A4, filed Oct. 16, 2002 by E. Ann Elsner) discusses a foldable head or chin-rest. However it does so very briefly without providing design details and only in the context of digital imaging of the retina and anterior segment. It does not discuss optical coherence tomography/optical coherence domain reflectometry (OCDR). Proposed design is more detail, generic and all-inclusive of various ophthalmic modalities.

SUMMARY

The invention discloses a foldable system, and a foldable apparatus for ophthalmology. The apparatus and system can be used for diagnosis, evaluation or therapy. The device can be used for ophthalmic imaging and/or diagnosis, anterior segment imaging and/or diagnosis, retinal imaging and/or diagnosis. The apparatus and system can be used for the eyes of the humans as well as the animals. In the proposed system, the chin-rest can be folded to save the space when the device is not in operation. This saves space while the device is in storage or under transportation.

In one embodiment, the apparatus or system comprises of an ophthalmic system comprising of at least one means to hold the face of a patient (i.e., face-holder), a diagnostic component to perform diagnosis or evaluation of the eye or a therapeutic component for the treatment of the eye and the means to fold the face-holder. Such a device can be termed as a "foldable face-holder apparatus" or a "foldable face-holder system".

In another embodiment, the face-holder can be folded at least once and possibly multiple times.

In another embodiment the face-holder comprises of a resting pad to rest the forehead (i.e., forehead rest).

In another embodiment, the face-holder comprises of a resting pad to rest the chin (i.e., chin-rest).

In another embodiment, the face-holder can be folded by collapsing multi-stage telescopic legs.

In another embodiment, the face-holder comprises of a chin-rest and a forehead rest and only the portion between the chin-rest and the instrument base is collapsible using multi-stage telescopic legs.

In another embodiment, the face-holder comprises of a chin-rest and a forehead rest and only the portion below the chin-rest and the instrument base is collapsible using multi-stage telescopic legs.

In one more embodiment, there is a folding hinge at or near the chin-rest.

In an embodiment, there is a folding hinge for the face holder at or near the instrument base.

In another embodiment, the proposed ophthalmic system comprises of at least one means to hold the face of a patient (i.e., face-holder) and the means to eject or remove the face-holder from the base of the instrument.

In another embodiment, the chin-rest can be removed or ejected using a button from the base of the instrument.

In another embodiment, the chin-rest is attached to the base of the instrument. In some other embodiments, the chin-rest-attachment is removable.

In another embodiment, the chin-rest is attached to the pole of the face-holder. and the chin-rest can be ejected or removed from the pole of the face-holder.

In one more embodiment, an ophthalmic system comprises of at least one means to hold the face of a patient (i.e., face-holder), an ocular diagnostic or therapeutic component and the means to remove the face-holder from the instrument and attach it to the patient's face.

In another embodiment, the face-holder is attached to the eyes using a head-band. In some embodiments, face-holder comprises of a chin-rest.

In some other embodiments, the face-holder is attached to the eyes using spectacles-type assembly. The eye-piece may be moved from one eye to the other for analyzing both the eyes.

In some embodiments, the chin-rest and/or the face-holder can slide in and out from the side of the ophthalmic system's base.

In some embodiments, the chin-rest and/or the face-holder can be folded completely and slides in the instruments' system's side.

In some embodiments, the apparatus or the system comprises of ophthalmic imaging.

In some other embodiments, the apparatus or the system comprises of optical coherence tomography (OCT) imaging.

In some other embodiments, the foldable face-holder apparatus or system comprises of optical coherence tomography (OCT) imaging apparatus/system and the OCT apparatus/system comprises of a spectrometer to implement spectral-domain OCT.

In some other embodiments, the foldable face-holder apparatus comprises of optical coherence tomography (OCT) imaging apparatus/system and the OCT apparatus/system comprises of a tunable wavelength (or frequency) light source to implement swept-source OCT or optical frequency domain reflectometry (OFDR).

In some other embodiments, the foldable face-holder apparatus or system comprises of optical coherence tomography (OCT) imaging apparatus/system and the OCT apparatus/system comprises of a depth-scanning reference mirror to implement time-domain OCT.

In one embodiment, the OCT system and apparatus mentioned above comprises of a light source of specific bandwidth, isolator, beam splitter, optical delivery unit, specimen, a grating, a detector array and a processor containing specific algorithms for signal and/or image processing.

In another OCT embodiment, as an additional feature, a polarization compensator is added to the basic configuration mentioned above. In one embodiment, a fiber stretcher is added in the basic configuration. The fiber stretcher is used to adjust the path-length in the corresponding arm of the system.

In one embodiment, the foldable system comprises of an OCT system comprising of a light source, provides a broad band light (of specific bandwidth) for acquiring an image from the subsurface area of a specimen. The specimen may be, but not limited to a moving sample, a stationary sample or a combination of both. The specimen may be a human or an animal eye or a device similar to an eye. In another embodiment, the system is modular so that a user can add off-the-shelf products to enhance the system capabilities. In another embodiment, several combinations of the basic configuration and additional components may be added to enhance the performance of the apparatus as a system as shown in the various figures that accompany this application, but not limited to only those.

In another embodiment, specific algorithm(s) reside in a processor in the foldable system to create an OCT image. The processor uses the algorithms such as the frequency resampling, demodulation, dispersion compensation, and Doppler processing to produce highly sensitive and high quality images. In another embodiment, the system performs spectroscopic detection. The resultant spectra are analyzed by the processor using inverse Fourier transformation and relevant signal processing for obtaining depth dependent (i.e. axial) reflectivity profile called A-scan. In another embodiment, two dimensional tomographic images, B-scan, are created from a sequence of axial reflectance profiles acquired by scanning the specimen.

In one embodiment, the foldable system may comprise of an OCT/OCDR sub-system comprising of a light source, an isolator, a processor, a fiber stretcher, a source arm, a reference arm, a sample arm, a detection arm, a beam splitter, a detector array, a grating unit, an optical delivery unit which can be folded, and a specimen (e.g., an eye) for analysis.

In some embodiments, bulk of the OCT/OCDR sub-system, e.g., light source, an isolator, a processor, a fiber stretcher, a source arm, a reference arm, a sample arm, a detection arm, a beam splitter, a detector array, a grating unit resides in the base of the foldable system.

In another embodiment, an OCT/OFDR sub-system may comprise of a tunable light source, an isolator, a processor, a fiber stretcher, a source arm, a reference arm, a sample arm, a detection arm, a beam splitter, a detector, an analog-to-digital converter, an optical delivery unit, and a specimen (e.g., human or animal eye) for analysis. In some embodiments, a polarization compensator may be used on the sample and/or reference arm. In some embodiments, the bulk of the OFDR/OCT components reside in the base of the foldable system.

In another embodiment, the OCT/OCDR sub-system enables a user to adjust the reference arm and the sample arm in order to adjust the path-lengths and/or polarization of the light beam to get a better quality image.

In another embodiment, light from a broadband light source operating at a suitable center wavelength is sent to an isolator, and then to the beam splitter using the source arm of the OCT sub-system. In another embodiment, the beam splitter splits the broadband light into two parts. One part of the light beam goes to the reference mirror using the fiber stretcher (on the reference arm) and other beam goes to the specimen using the sample arm.

In some other embodiments, the apparatus/system comprises of means to shift the eye-piece (which is optics used to focus on the eye) towards the left or right eye.

In some embodiments, the eye-piece is shifted using a precision slide.

In some other embodiments, the eye-piece is shifted using a sliding rod.

In some embodiments, the eye-piece is positioned using a micro-precision slide.

In some embodiments, the foldable face-holder apparatus/system comprises of the means for an eye-fixation target.

In some embodiments, the apparatus/system comprises of fiber or cables running from the instrument to the eye.

In another embodiment, the OCT sub-system mentioned above has also at least one of a fractional wave mirror, waveplate (e.g., $\lambda/8$), a fiber-optic mirror and a free space mirror.

In some embodiments, the apparatus/system comprises of a screen to display measurement or imaging results.

In some other embodiments the display screen is a touch-sensitive screen.

In some embodiments, the base of the apparatus/system comprises of electronics and optical components.

In some embodiments, all the apparatus or system components reside in a brief-case or a suit-case or a box or a tablet (e.g., an iPad or android tablet)-size unit.

In some embodiments, the brief-case has wheels and/or a handle to assist transportation.

In some embodiments, the apparatus/system operates on batteries. In some other embodiments, these batteries can be rechargeable batteries. The batteries can be charged independently or by connecting a charger to the apparatus/system. The charger can source power from the electrical wiring in a building or any other power source. The charger can also source power from a vehicle such as a car or a bus or a truck or a van. The charger can also source the power from the vehicle's engine.

In some embodiments, the apparatus/system evaluates or scans the retina and/or the posterior segment. In some other embodiments, the apparatus/system evaluates or scans the cornea and/or anterior segment.

DETAILED DESCRIPTION

The instant disclosure describes a technological advancement of foldable ophthalmic apparatus and system. Such a system would be compact, portable and would save storage space.

Figure 1:
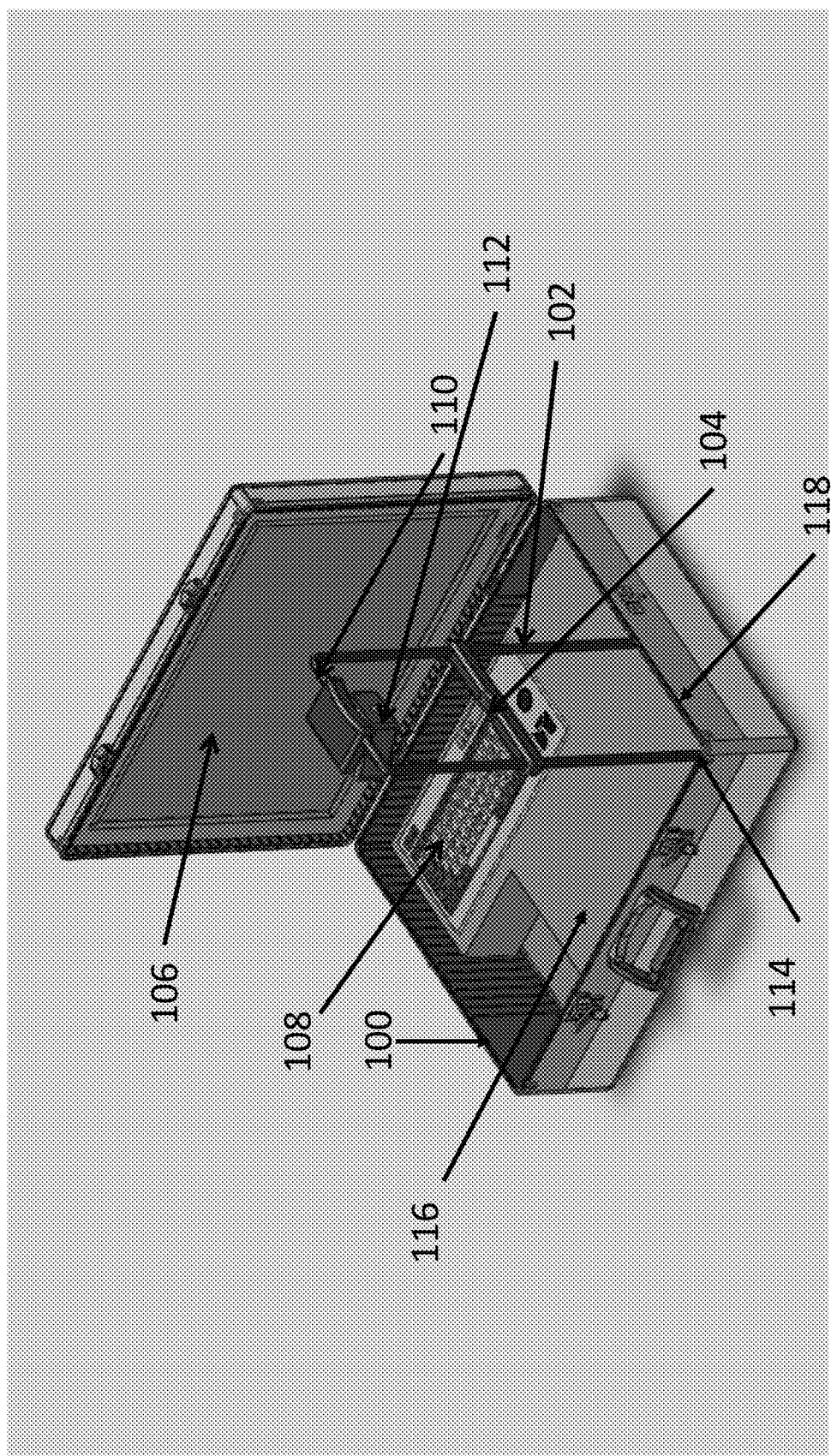
FIG. 1 depicts a simplified version of the foldable ophthalmic apparatus/system 100.

FIG. 1 depicts a simple version of the foldable face-holder apparatus/system 100. The apparatus/system comprises of an ophthalmic system comprising of at least one means to hold the face of a patient (i.e., face-holder 102), a diagnostic component to perform diagnosis or evaluation or a therapeutic component to perform treatment of the eye and the means to fold the face-holder (e.g., hinge 114). Thus the apparatus and system will comprise of at least one of diagnostic, evaluation and therapeutic components.

The diagnostic, evaluation and/or therapeutic components can direct light to the eye (and receive the back-scatter from the eye) using an optical delivery unit. In some embodiments, the optical delivery unit is a part of the face-holder.

In some embodiments, the face-holder can be folded at least once and possibly multiple times. In some embodiments, the face-holder comprises of a resting pad to rest forehead (i.e., forehead rest 110). In another embodiment, the face-holder comprises of a resting pad to rest chin (i.e., chin-rest 104).

Figure 3:
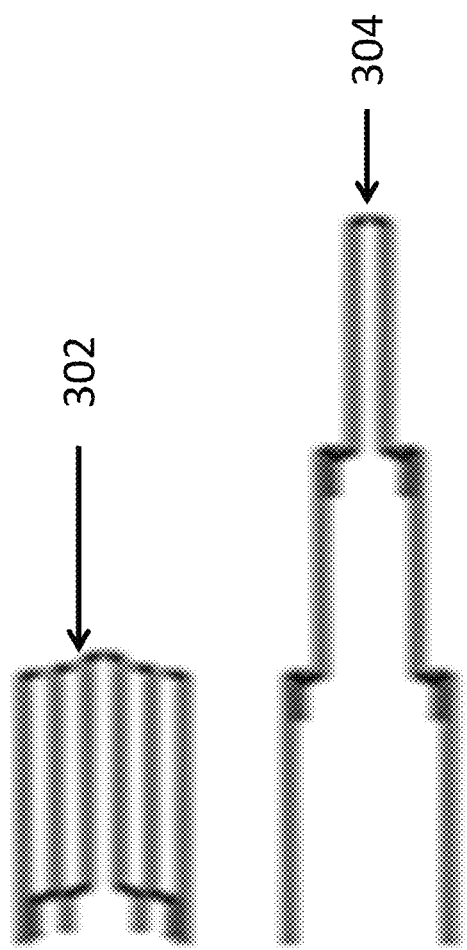
FIG. 3 illustrates telescopic legs.

In another embodiment of the instant apparatus or system, the face-holder can be folded by collapsing multi-stage telescopic legs. In another embodiment, the face-holder comprises of a chin-rest 104 and a forehead rest 110 and only the portion between the chin-rest 104 and the instrument base 118 is collapsible using multi-stage telescopic legs (FIG. 3).

In some other embodiments, the apparatus/system comprises of an eye-piece 112 which is optics and mechanics used to evaluate or treat the eye. In some embodiments, the eye-piece is a part of the optical delivery unit.

In some embodiments, the apparatus/system comprises of a screen 106 to display measurement or imaging results. Thus, the display can host diagnostic-assisting results. In some other embodiments the display screen 106 is a touch-sensitive screen. In some other embodiments, the display could have 3-D capabilities (or stereoscopic capabilities) showing 3-dimensional features of the data or the measurements or anatomic features.

In some embodiments, the apparatus/system comprises of a keyboard 108 to control the apparatus/system. The keyboard 108 can optionally comprise of a mouse or a controlling ball or a joystick. In some other embodiments the keyboard 108 is a touch-sensitive screen. In some embodiments, the touch-sensitive display comprises of the keyboard.

In some embodiments, the eye-piece is shifted using a precision slide to evaluate or treat the left or right eye. In some other embodiments, the eye-piece is shifted using a sliding rod. In some embodiments, the eye-piece is positioned using a micro-precision slide. In some embodiments, the eye-piece is a part of the optical delivery unit.

In some embodiments, the eye-piece has railings to move it forward and/or backward with respect to the patient's eye.

In some embodiments, the foldable face-holder apparatus/system comprises of the means for an eye-fixation target. These means could comprise of a display inside the eye-piece 112. The display could have an eye-fixation target as desired by the operator of the apparatus/system.

In some embodiments, the base 118 of the apparatus/system comprises of electronics and optical components. In some other embodiments of the invention, the apparatus/system comprises of fibers or cables running from the base 118 to the eye-piece 112.

Figure 2:
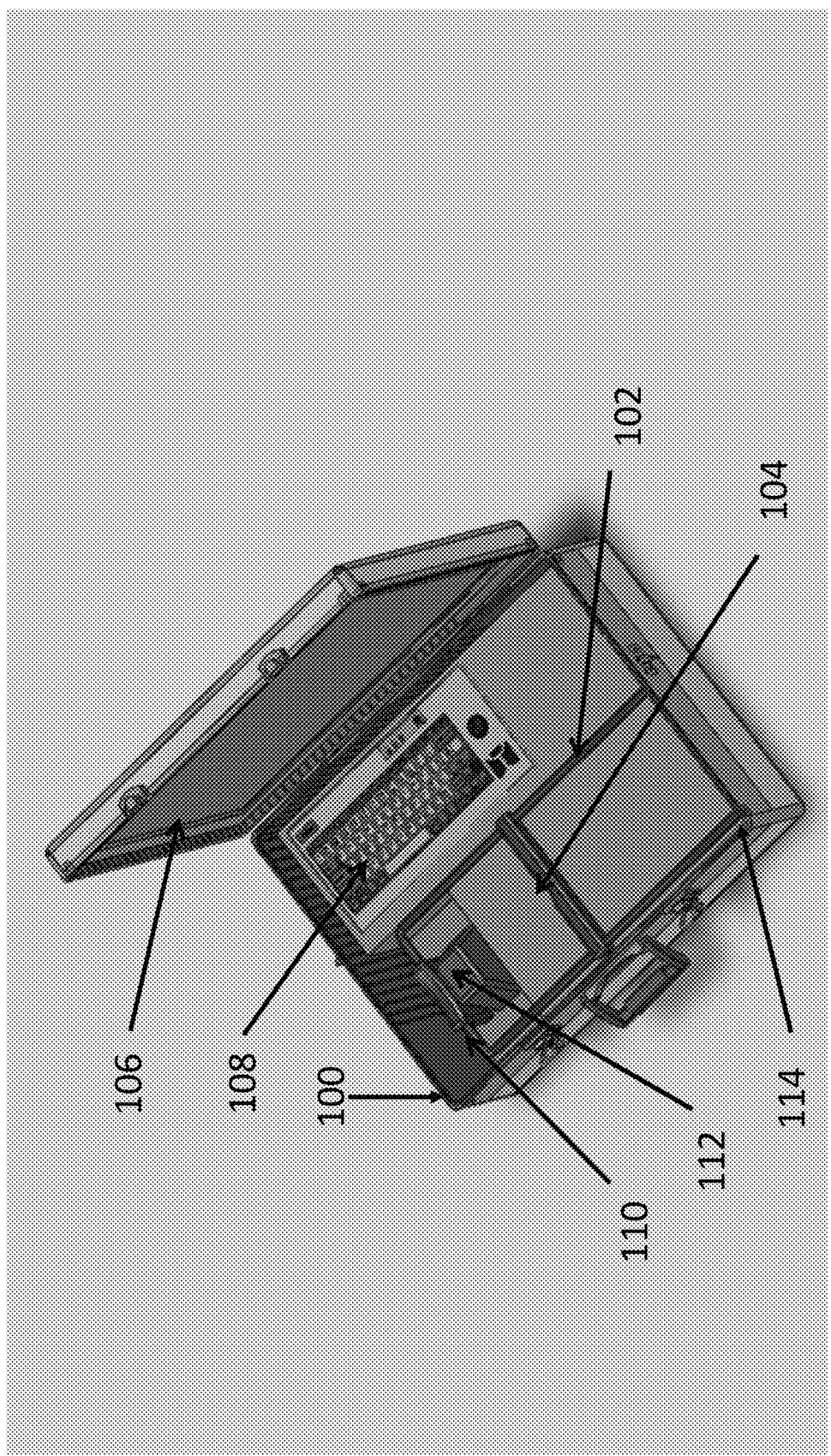
FIG. 2 depicts the folded version of the foldable ophthalmic apparatus/system 100.

FIG. 2 depicts the folded version of the foldable face-holder apparatus/system 100. It is folded at the hinge 114. In some embodiments, the face-holder can be folded at least once and possibly multiple times. In another embodiment of the instant apparatus/system, the face-holder can be folded by collapsing multi-stage telescopic legs. In another embodiment, the face-holder comprises of a chin-rest 104 and a forehead rest 110 and only the portion between the chin-rest 104 and the instrument base 118 is collapsible using multi-stage telescopic legs as illustrated in FIG. 3. The collapsed legs are shown as 302 and elongated legs are shown as 304 in FIG. 3.

In one more embodiment, there is a folding hinge 114 at or near the chin-rest 104.

In another embodiment, the proposed ophthalmic system comprises of at least one means to hold the face of a patient (i.e., face-holder) and the means to eject (using a button) or remove the face-holder from the base of the instrument.

In another embodiment, the chin-rest can be removed or ejected from the base of the instrument. In another embodiment, the chin-rest is attached to the base of the instrument. In some other embodiments, the chin-rest-attachment is removable.

In some embodiments, all the apparatus/system components reside in a brief-case as shown in FIG. 1. In some embodiments, the brief-case has wheels and/or a handle to assist transportation.

In some embodiments, the apparatus/system operates on batteries. In some other embodiments, these batteries can be rechargeable batteries. The batteries can be charged independently or by connecting a charger to the apparatus. The charger can source power from the electrical wiring in a building. The charger (termed a vehicle charger) can also source power from a vehicle such as a car or a bus or a truck or a van. The charger can also source power from the vehicle's engine.

In some embodiments, the apparatus/system could comprise of a projector (sometimes termed pico-projector) to display the results or the images or the data on a wall or a screen.

In some embodiments, the apparatus is used for ophthalmic imaging. Ophthalmic imaging includes (but does not limit to) retinal imaging and anterior segment.

OCT/OCDR/OFDR Sub-System Description

In some other embodiments, the foldable ophthalmic apparatus/system comprises of optical coherence tomography (OCT) imaging. Optical coherence domain reflectometry (OCDR) is a 1-dimensional measurement system and OCT is a 2-D extension of OCDR. Since OCT and OCDR are similar, sometimes we would refer these as OCT-OCDR systems. The diagnostic components or systems based on OCT-OCDR, will be called as OCT-OCDR based diagnostic components.

Optical coherence tomography (OCT) and OCDR are very similar to ultrasound imaging. OCDR-OCT provides cross-sectional images of micro-features that are acquired from adjacent depth resolved reflectivity profiles of the tissue. OCT also employs a fiber optically integrated Michelson interferometer illuminated with a short coherence length light source such as a superluminiscent diode (SLD). The interferometric data are processed in a processor/computer and displayed as a gray scale image. In an OCDR-OCT image, the detectable intensities of the light reflected from human tissues range from $10^{-5}$ to $10^{-11}$ th part of the incident power.

In some other embodiments, the foldable face-holder apparatus or system comprises for optical coherence tomography (OCT) imaging apparatus/system and the OCT apparatus/system comprises of a spectrometer to implement spectral-domain OCT.

Figure 4:
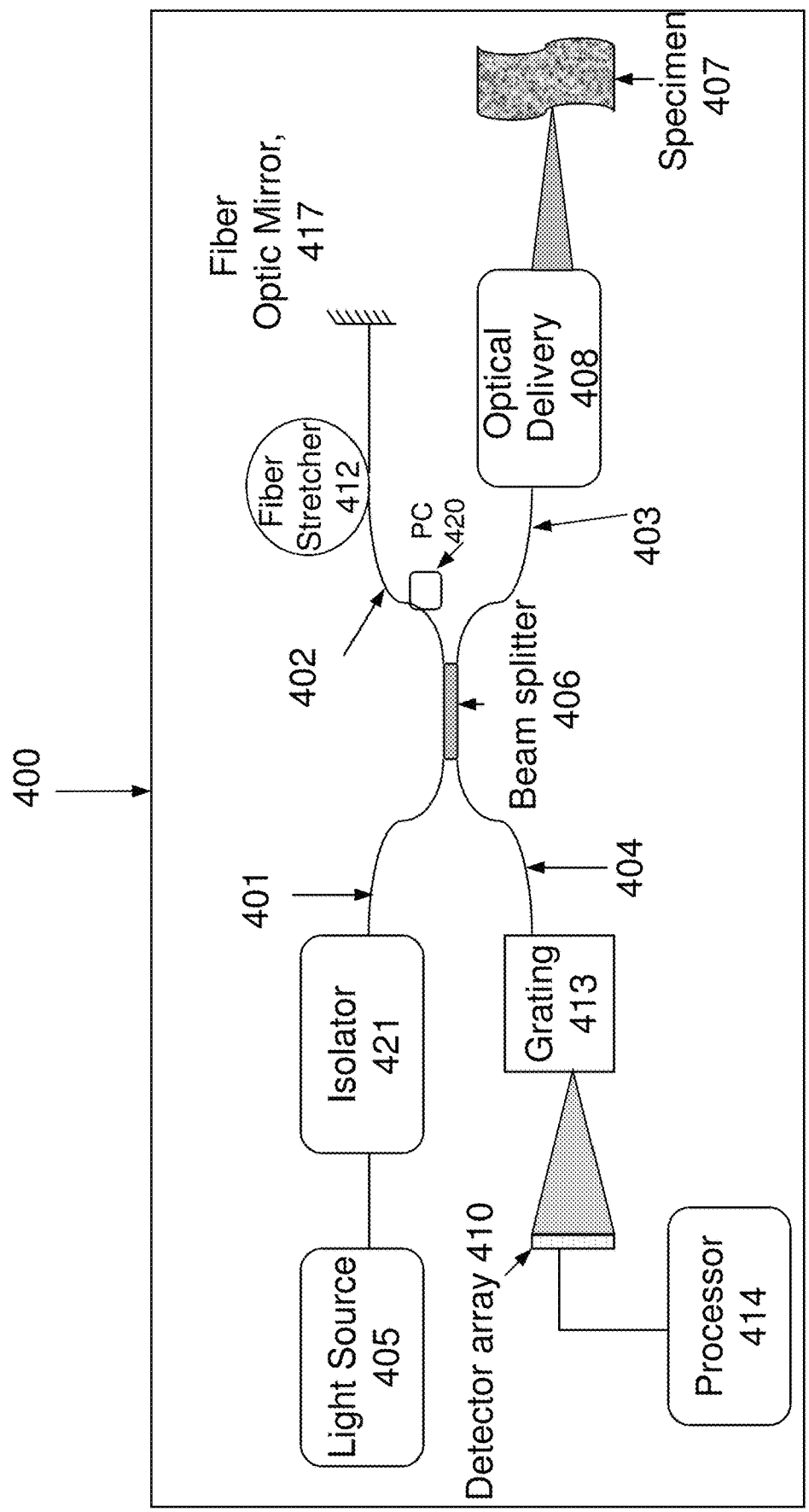
FIG. 4 is a block diagram of an OCDR-OCT sub-system 400 (which can be incorporated into a foldable ophthalmic system), in accordance with an embodiment of the present invention; the key elements being a grating unit, a fiber optic mirror, and a fiber stretcher.

OCDR-OCT System: FIG. 4 shows an OCDR-OCT system 400 comprising of a light source 405 of a specific bandwidth, isolator 421, processor 414, fiber stretcher 412, source arm 401, reference arm 402, sample arm 403, detection arm 404, beam splitter 406, detector array 410, a grating unit 413, optical delivery unit 408, fiber optic mirror 417 and a specimen 407 (could be a human or an animal eye) for analysis.

In some embodiments, the optical delivery unit 408 is further integrated with the face-holder of the folding ophthalmic system.

A light source 405, in a system or as a part of the apparatus/system, may comprise of off-the-shelf light sources.

The center wavelength ($\lambda_0$) most ideal for the retinal applications range from 750 nm till 1050 nm. Water (and aqueous humor) absorption is minimal for this wavelength range. The power for retinal applications ranges from 0.1 mW to 10 mW. Per ANSI safety standards only 0.75 mW are permitted incident on the eye at this wavelength range of 750 nm till 850 nm. The center wavelength most ideal for the non-retinal applications (e.g., skin, anterior segment of the eye, gastrointestinal tract, lungs, teeth, blood vessels, subsurface area of semi-conductors, chip manufacturing, sensitive medical equipment's etc.) range from 1050 nm till 1350 nm. The longer wavelength is more suitable for thick scattering tissues since scattering is less at higher wavelengths. The system depth resolution (DR) is inversely proportional to the FWHM spectral width (or bandwidth$\Delta\lambda$) of the light source spectrum. It is given by the following equation:

$$DR = \frac{2\ln 2}{\pi} \frac{\lambda_0^2}{\Delta\lambda} \qquad (\text{Eq 1})$$

The full-width-half-max (FWHM) spectral width of the light source typically ranges from 10 nm till 150 nm. The power for non-retinal applications ranges from 0.1 mW till 30 mW in the wavelength range from 1050 nm till 1350 nm. The full-width-half-max (FWHM) spectral width of the light source typically ranges from 10 nm till 150 nm.

The light source 405 may be electrically operated. These can be battery operated while in transit. The forward voltage typically ranges from 2 to 10 Volts. The forward current typically ranges from 100 mA to 1 A. Some of these sources need to be thermo-electrically controlled (TEC). The operating internal temperature for some sources is typically 25° C. The corresponding thermistor resistance is 10 kilo-Ohms (10 k$\Omega$). Typical TEC current is 1.5 A. Typical TEC voltage is 3-4V. The light source may also be tunable light source as shown in other system/apparatus embodiments.

The isolator 421 protects the light source from back reflections and permits the transmission of light in the forward direction with a limited loss. The fiber-optic isolator used in device would need to operate on a broad range of spectrum to cover the full spectral-width of the light source (Depending upon the source spectral shape, typically 2*FWHM bandwidth $\Delta\lambda$). Thus the operating wavelength range is $\lambda_0$+/-$\Delta\lambda$. Typical isolation is 20-40 dB, and insertion loss is 0.5-3 dB. The polarization dependent loss is typically 0.5 dB or less. Return loss is typically more than 40 dB.

The isolator 421 comprises of an input linear polarizer, a ($\lambda$/8) Faraday rotator or a waveplate, and an output linear polarizer. The ($\lambda$/8) Faraday rotator or a waveplate rotates the light transmitted through the input polarizer by 45 degrees. The output polarizer needs to have the same direction as "the input polarizing direction rotated by 45 degrees" in order to have the maximum transmission and maximum isolation. The light returning to the isolator from the remaining system gets linearly polarized by the output polarizer and is rotated by 45 degrees, making it orthogonally polarized as compared to the input polarizing direction. Thus, the returning light is totally absorbed.

Fiber stretcher 412 comprises of a fiber looped around a piezoelectric device (which is a solid block that can be expanded or contracted by electric voltage). The fiber stretcher is not strictly necessary in an OCDR/OCT system, it can be optionally used. The purpose of a fiber stretcher is to increase or decrease the path-length in the interferometer by increasing or decreasing the fiber-length. Although the fiber stretcher 412 is shown in the reference arm, it can be placed ether in the reference arm or sample arm. If the fiber stretcher 412 is kept in the reference arm, since the fiber is looped around the piezoelectric device, care must be taken to provide extra fiber in the sample arm so that the sample arm and reference arm path lengths are matched.

The fiber optic mirror 417 is situated on the tip of the fiber.

Bulk of the components of the OCT/OCDR system can be placed in the base of the foldable ophthalmic system in some embodiments. The optical delivery unit 408 in the sample arm can focus light on the eye, and can be folded as needed. The optical delivery unit 408 can be attached to the face holder in some embodiments.

Detector array 410 is a line-scan camera. It has typically 1024-4096 pixels, though the proposed embodiment is not limited to these numbers. Typically it is a CCD or CMOS camera. Line-rate (rate of acquisition of arrays) is typically 10000 lines/s to 400000 lines/s, though the proposed embodiment is not limited to these numbers. Each pixel outputs a value which typically has an 8-bit or 12-bit format, though the proposed embodiment is not limited to these numbers. The pixel size is typically 14 microns (height) and 14 microns (width). The light dispersed by the grating is focused on the detector array to generate the light spectrum. The output of the array (line-scan camera) is typically directed to the computer using an Ethernet cable (e.g., Gigabit Ethernet) or a USB (typically 2.0 or 3.0) cable, etc. The operating wavelength ranges from 400 nm to 1100 nm for retinal applications. The above numbers and examples are given for illustrative purposes only, the proposed embodiment is not limited to these numbers or examples.

The beam splitter 406 (made of fiber optics) splits the light typically into 50/50. It is built using two fused single-mode fibers. The fiber for retinal applications (~800 nm wavelength) has 4-6 microns core diameter and 125 microns cladding diameter, 0.130 core numerical aperture (NA), cutoff wavelength of typically 730 nm. The insertion loss (in addition to designed 3 dB or 50% loss) is typically 0.3 dB. For the couplers used for OCT, the length of the fiber in the reference and sample arms is very important and the lengths are specified with tight tolerances.

The waves reflected back from the sample arm 403 and the reference arm 402 interfere at the detector array 410. Since the interference signal is only created when the polarization in the reference arm 402 matches with that in the sample arm 403, in some embodiments, a polarization compensator 420 is used either in the reference arm or the sample arm. Polarization compensator 420 is also known as fiber optic polarization compensators. In some embodiments, the compensator comprises of 3 coils of fiber on 3 different paddles arranged in a series. The first fiber coil is a quarter wave plate, the second fiber coil is a half wave plate (typically the fiber is looped around twice for the same paddle diameter as the first paddle), the last fiber coil is a quarter wave plate. These 3 paddles can be rotated freely with respect to each other to produce any polarization state.

There is another type of polarization compensator, which applies pressure to the fiber to create birefringence. The slow axis is in the direction of the pressure applied. This fiber squeezer can be rotated around the fiber to rotate the direction of the slow axis. Thus, any arbitrary polarization can be created.

In some embodiments of the OCT systems, light exits a fiber tip in the reference arm and the light returns from a retro reflecting mirror mounted in the air.

OCDR-OCT sub-system uses spectroscopic detection method. Basically the interferometric light exiting the detector arm 403 is dispersed via a grating. The spectra are acquired using a line-scan camera. The resulting spectra are typically (by way of example, not by limitation) transferred to a processor for inverse Fourier transforming and relevant signal processing (such as obtaining the complex envelope of the interferometric signal) for obtaining depth dependent (i.e., axial) reflectivity profiles (A-scans). The axial resolution is governed by the source coherence length, typically ~3-10 μm. Two dimensional tomographic images (B-scans) are created from a sequence of axial reflectance profiles acquired while scanning the probe beam laterally across the specimen or biological tissue.

A-scan: A-scan is a plot of reflectivity of scatterers and layers as a function of depth at a given lateral location. It is computed as follows:
a) The interferometric light exiting the detector arm is dispersed via a grating.
b) The dispersed light has a spectrum which is focused on a detector array or a line-scan camera. Thus, the grating unit disperses the partial returning light from the beam splitter and a dispersed light enters the detector array to produce a light spectrum.
c) The recorded spectra are typically transferred to a processor. The processor performs a data analysis using specific algorithms on the light spectrum.
d) An inverse Fourier transform of the spectrum is computed.
e) Relevant signal processing is performed (such as removing the duplicate data and strong spikes at the center of the inverse Fourier transform) using specific algorithms.
f) The resulting arrays are depth dependent (i.e., axial) reflectivity profiles (A-scans). Thus the system generates A-scans of the eye; if the eye is the specimen used in the system.
g) The axial resolution is governed by the source coherence length, typically ~3-10 μm.

B-scan: Two dimensional tomographic images (B-scans) are created from a sequence of axial reflectance profiles acquired while scanning the probe beam laterally across the specimen or biological tissue. The following are detail steps:
a) An A-scan is acquired at a given lateral location.
b) A mirror is scanned using a scanner such as a galvanometer or a MEMS mirror in the optical delivery unit.
c) Multiple A-scans are acquired at various lateral locations.
d) A matrix is generated where columns indicate different lateral locations and rows indicate reflectivity at each depth in each A-scan.
e) The matrix is displayed as an image, which is also a B-scan.

In some embodiments of this invention, the grating disperses light and a lens focuses it into a detector array 410. By way of example, but not by limitation, this array can be a line-scan camera, which has quantum efficiency p at the operating wavelengths. The resulting data set is inverse Fourier transformed, processed in a processor 414 and displayed as a gray scale or pseudo-color image. By way of example, not by limitation, this processor can be a computer, off-the-shelf integrated circuit, application specific integrated circuit (ASIC), Field Programmable Gate Array (FPGA), a graphical processing unit (GPU) an embedded system or a microcontroller.

Extensions of the proposed interferometer: An interferometric 2D imaging system (Optical coherence tomography or OCT) can be constructed using the proposed interferometric system where the 2D images are obtained by laterally scanning the beam incident on the sample using a 1-D scanning mirror (which is a part of the optical delivery unit). An interferometric 3D imaging system can be constructed using the proposed interferometric system where the 3D data-sets are obtained by 2D laterally scanning the beam incident on the sample using a 2-D scanning mirror (which is a part of the optical delivery unit).

Both the 2D imaging systems and 3D imaging systems can be adapted for ophthalmic imaging by using a lens assembly (which is a part of the optical delivery unit) to focus the light on the retina.

In some embodiments, the optical delivery unit is integrated with the face-holder of the foldable ophthalmic system.

An example lens assembly is described below (not as a limitation), but other lens assemblies could be used. The OCDR-OCT system can be adapted to measure retina by collimating the beam exiting the sample arm fiber, expanding the beam using a lens, shrinking the beam to project on the cornea, and the cornea and lens system of the eye will automatically focus the beam on the retina.

In some embodiments, a fractional wave mirror is placed at the end of the reference arm of the OCDR/OCT/OFDR system. The fractional wave mirror comprises of a fiber-optic mirror preceded by a fractional [45 degrees ($\lambda/8$)] waveplate. Here $\lambda$ indicates wavelength. The polarization of light incident on the wave plate is rotated by 45 degrees, and is directed to the fiber-optic mirror. The reflected light is further rotated by 45 degrees by the fractional [45 degrees ($\lambda/8$)] waveplate and hence the resulting polarization is orthogonal to the incident polarization. Polarization compensator 420 may not be necessary in this embodiment. A modified formula based on LeFevre is disclosed in this disclosure and which is as follows:

Mechanical stress on the fiber causes birefringence in the fiber. Stress can be generated by simply bending the fiber. According to LeFevre (U.S. Pat. No. 4,615,582), the fractional wave plate can be built by looping the fiber into N loops having a radius R. The refractive index difference $\Delta n$ for two orthogonal polarizations is given by $$\Delta n = b\left(\frac{r}{R}\right)^2 \quad \text{(Eq 2)}$$

b is a constant depending upon the photoelastic coefficient of the fiber, r is the radius of the fiber and R is the radius of the fiber loop. Thus, if we want to create a $\lambda/m$ (where m is an integer) waveplate, which will introduce a path-length shift of $\lambda/m$ between 2 polarizations, we'll need to create a loop of fiber length L to create the path-length shift of $\Delta nL$. However, since the length of the fiber is also equal to $2\pi NR$, where N is the number of loops, we get $$(2\pi NR)b\left(\frac{r}{R}\right)^2 = \frac{\lambda}{m} \quad \text{(Eq 2)}$$

or $$R = (2\pi mN)b\frac{r^2}{\lambda} \quad \text{(Eq 4)}$$

To create a fractional wave plate of $$\frac{\lambda}{8},$$

and N=1 (single loop), b=0.25, m=8, r=125 microns, $\lambda$=0.8 microns, we get $$R = (2\pi 8)0.25\frac{(125)^2}{0.8} = 5\pi * 15625 = 24.54 \text{ cm} \quad \text{(Eq 5)}$$

Please note that a $(2M+1)\lambda/m$ waveplate where M is an integer between $-\infty$ to $\infty$ will have a similar effect as a $\lambda/m$ waveplate. The corresponding equation is $$R = (2\pi mN)b\frac{r^2}{\lambda(2M+1)} \quad \text{(Eq 6)}$$

Thus, if M=5 in the example above; R would be 2.23 cm, leading to a more compact loop. We could choose various values of M leading to an optimal design and size.

The waves reflected back from the sample arm 403 and the reference arm 402 interfere at the detector array 410. Since the interference signal is only created when the polarization in the reference arm 402 matches with that in the sample arm 403, in some embodiments, one can include by way of example but not by limitation a 45 degrees $\lambda/8$ waveplate in the sample arm 403 just before the light is incident on the optical delivery unit 408. Since the polarization of the retro reflected light will be almost orthogonal to the incident light (considering the fact that the birefringence in the specimen 407 will modify the polarization state), the birefringence effects in the sample arm fiber 403 of the interferometer 400 will get cancelled. In an embodiment, the $\lambda/8$ waveplate is constructed using fiber optic components.

In another preferred embodiment, the $\lambda/8$ waveplate is a fractional-waveplate constructed using fiber optic components. It would be constructed in the optical delivery unit near the end of the fiber segment in the optical delivery unit. The fractional waveplate is located on the sample arm of the apparatus/system. It may be made an integral part of the optical delivery 408. The fractional wave mirror in the reference arm comprises of a fiber-optic mirror preceded by a fractional [45 degrees ($\lambda/8$)] waveplate. The polarization of the light incident on the waveplate is rotated by 45 degrees, and is directed to the mirror. The reflected light is further rotated by 45 degrees by the fractional [45 degrees ($\lambda/8$)] waveplate and hence the resulting polarization is orthogonal to the incident polarization. In another embodiment, a free-space-bulk 45 degrees ($\lambda/8$) wave plate is used at the end of the optical delivery unit. Polarization compensator 420 may not be necessary in these embodiments.

In some embodiments, the optical delivery unit 408 in the sample arm is integrated with the foldable face-holder.

Figure 5:
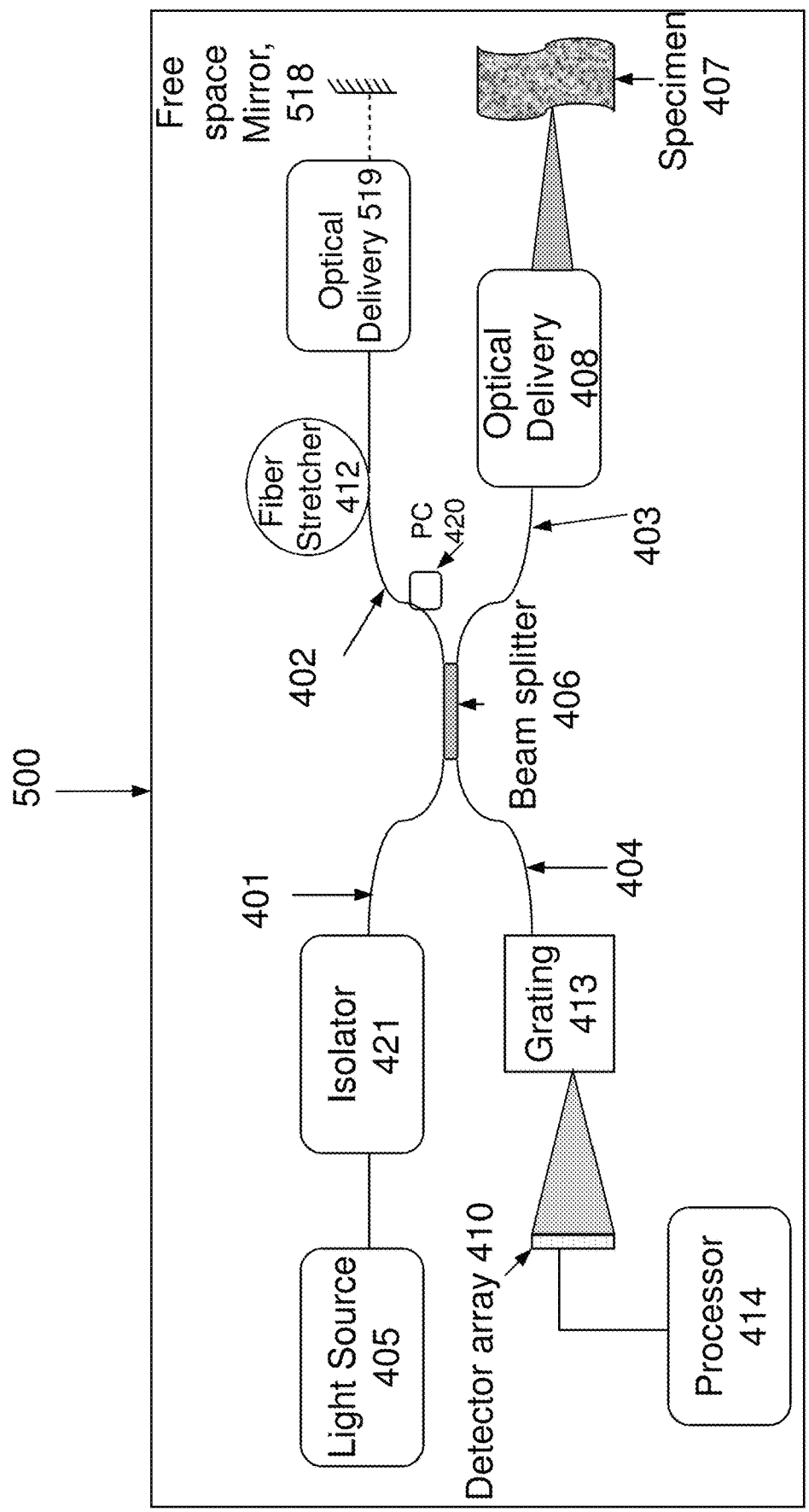
FIG. 5 is a block diagram of the OCDR-OCT system 500 (which can be incorporated into a foldable ophthalmic system) similar to that in FIG. 4 except that the fiber optically integrated mirror is replaced by a free space mirror.

In another variation of this embodiment (system 500 in FIG. 5), the fiber optically integrated mirror can be replaced by a free space mirror 518. The light can be delivered to the mirror using optical delivery unit 519. FIG. 5 has standard free-space-mirror 518 in the reference arm, which still permits use of instant algorithms such as frequency resampling, dispersion compensation, and Doppler processing algorithms. In some embodiments, the foldable face-holder comprises of the optical delivery unit 408 in the sample arm.

In some other embodiments, the foldable face-holder system is used for optical coherence tomography (OCT) imaging and the OCT system comprises of a tunable wavelength (or frequency) light source to implement swept-source OCT or optical frequency domain reflectrometry (OFDR) (as described in S R Chinn, E A Swanson, J G Fujimoto—Optics Letters, 1997; M A Choma, M V Sarunic, C Yan et al—Optics Express, 2003; Y Yasuno, V D Madjarova, S Makita, M Akiba et al—Optics Express 2005).

Frequency Domain OCT or swept source OCT or Optical Frequency Domain Reflectrometry (OFDR): In some OCT sub-systems such as frequency domain OCT or swept source OCT or Optical Frequency Domain Reflectrometry (OFDR), the broad-band light source is replaced by a tunable frequency light source. The detector array is replaced by a single detector. The use of a grating is not needed for this embodiment. In this embodiment (system 600 in FIG. 6), a fiber-optically integrated mirror 417 in the reference arm 402 of the OFDR-OCT system 600 can be used. Tunable light source 602 in this embodiment is applicable to FIG. 6-8 only. The center wavelength most ideal for the retinal applications range from 750 nm till 1050 nm. The wavelength of the source is tuned very rapidly (e.g., at a rate of 10 kHz-10 MHz) within a spectral range of typically 10 to 100 nm around the center wavelength. The average power of such a source typically ranges from 0.1 mW to 20 mW depending upon the applications. The source may be electrically operated. The existing commercially available sources operate on 110/220V 50/60 Hz power input. In future, these could be operated using lower voltages and battery operated while in transit. ADC 624 is added so that the electrical current is transformed.

In this embodiment there is no grating 413 and detector array. Instead a Detector 622 is added. It is a photo-diode (which converts light into electricity). The detectors for 300-1000 nm are typically made up of silicon. The detectors for 900-1700 nm are typically made up of InGaAs. These are high-speed detectors with typically 0 to a few hundred MHz bandwidth. In some embodiments more than one detector may be used to achieve dual-balanced detection. It is typically followed by a high-speed A/D (analog to digital) converter (ADC) 624, e.g., 8-bit or 12-bit with a conversion rate of 1 to 20000 Mega Samples/second. The detector(s) direct(s) the signal to the ADC to generate a digitized signal. Typical responsivity of photodiodes is 0.1-1 mA/mW. The output voltages are typically −5 to 5V, with typical 50Ω impedance. These assist in achieving typical line-rates (rate of acquisition of A-scans) of 10000 lines/s to 400,000 lines/s (can be higher than 10 M lines/s in very high speed lasers). The digitized output of the A/D converter is typically directed to a computer or a processor using an Ethernet cable (e.g., Gigabit Ethernet) or a USB (typically 2.0 or 3.0) cable, or directly attached to the computer's PCI (Peripheral Controller Interface) bus etc. The processor generates A-scans and/or B-scans.

Since the interference signal is only created when the polarization in the reference arm 402 matches with that in the sample arm 403, in some embodiments, a polarization compensator 420 is used either in the reference arm or the sample arm. Polarization compensator 420 is also known as fiber optic polarization compensator. In some embodiments, the compensator comprises of 3 coils of fiber on 3 different paddles arranged in a series.

In some embodiments, a fractional wave mirror (as described earlier) is placed at the end of the reference arm of the OCT/OFDR system. The fractional wave mirror comprises of a fiber-optic mirror preceded by a fractional [45 degrees (λ/8)] waveplate. Here λ indicates wavelength. The polarization of light incident on the wave plate is rotated by 45 degrees, and is directed to the fiber-optic mirror. The reflected light is further rotated by 45 degrees by the fractional [45 degrees (λ/8)] waveplate and hence the resulting polarization is orthogonal to the incident polarization. Polarization compensator 420 may not be necessary in this embodiment.

The waves reflected back from the sample arm 403 and the reference arm 402 interfere at the detector array 410. Since the interference signal is only created when the polarization in the reference arm 402 matches with that in the sample arm 403, in some embodiments, one can include by way of example but not by limitation a 45 degrees λ/8 waveplate in the sample arm 403 just before the light is incident on the optical delivery unit 408 in the OCT/OFDR system. Since the polarization of the retro reflected light will be almost orthogonal to the incident light (considering the fact that the birefringence in the specimen 407 will modify the polarization state), the birefringence effects in the sample arm fiber 403 of the interferometer 400 will get cancelled. In an embodiment, the λ/8 waveplate is constructed using fiber optic components. Polarization compensator 420 may not be necessary in this embodiment.

In another preferred embodiment, the λ/8 waveplate is a fractional-waveplate constructed using fiber optic components in the OCT/OFDR system. It would be constructed in the optical delivery unit near the end of the fiber segment in the optical delivery unit. The fractional waveplate is located on the sample arm of the apparatus/system. It may be made an integral part of the optical delivery 408. The fractional wave mirror in the reference arm comprises of a fiber-optic mirror preceded by a fractional [45 degrees (λ/8)] waveplate. The polarization of the light incident on the waveplate is rotated by 45 degrees, and is directed to the mirror. The reflected light is further rotated by 45 degrees by the fractional [45 degrees (λ/8)] waveplate and hence the resulting polarization is orthogonal to the incident polarization. In another embodiment, a free-space-bulk 45 degrees (λ/8) wave plate is used at the end of the optical delivery unit. Polarization compensator 420 may not be necessary in this embodiment. The foldable face holder comprises of the optical delivery unit 408 in some embodiments.

Figure 6:
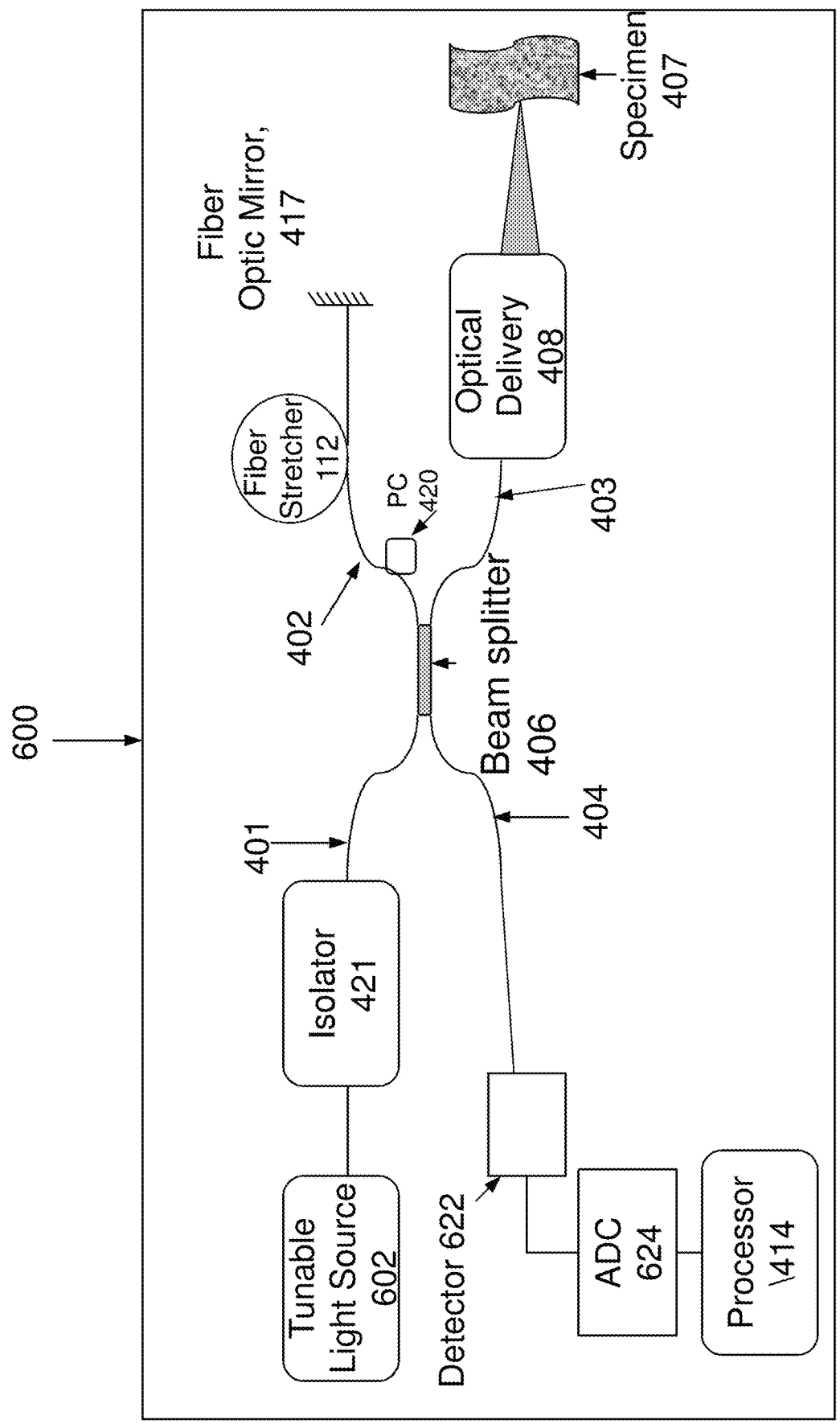
FIG. 6 is a block diagram of the OFDR (optical frequency domain reflectometry)-OCT system 600 (which can be incorporated into a foldable ophthalmic system) similar to that in FIG. 4 except that the broad-band source is replaced by a tunable frequency source, detector array is replaced by a single high-speed detector, and the diffraction grating is eliminated. Such a system is called swept-source OFDR/OCT.
Figure 7:
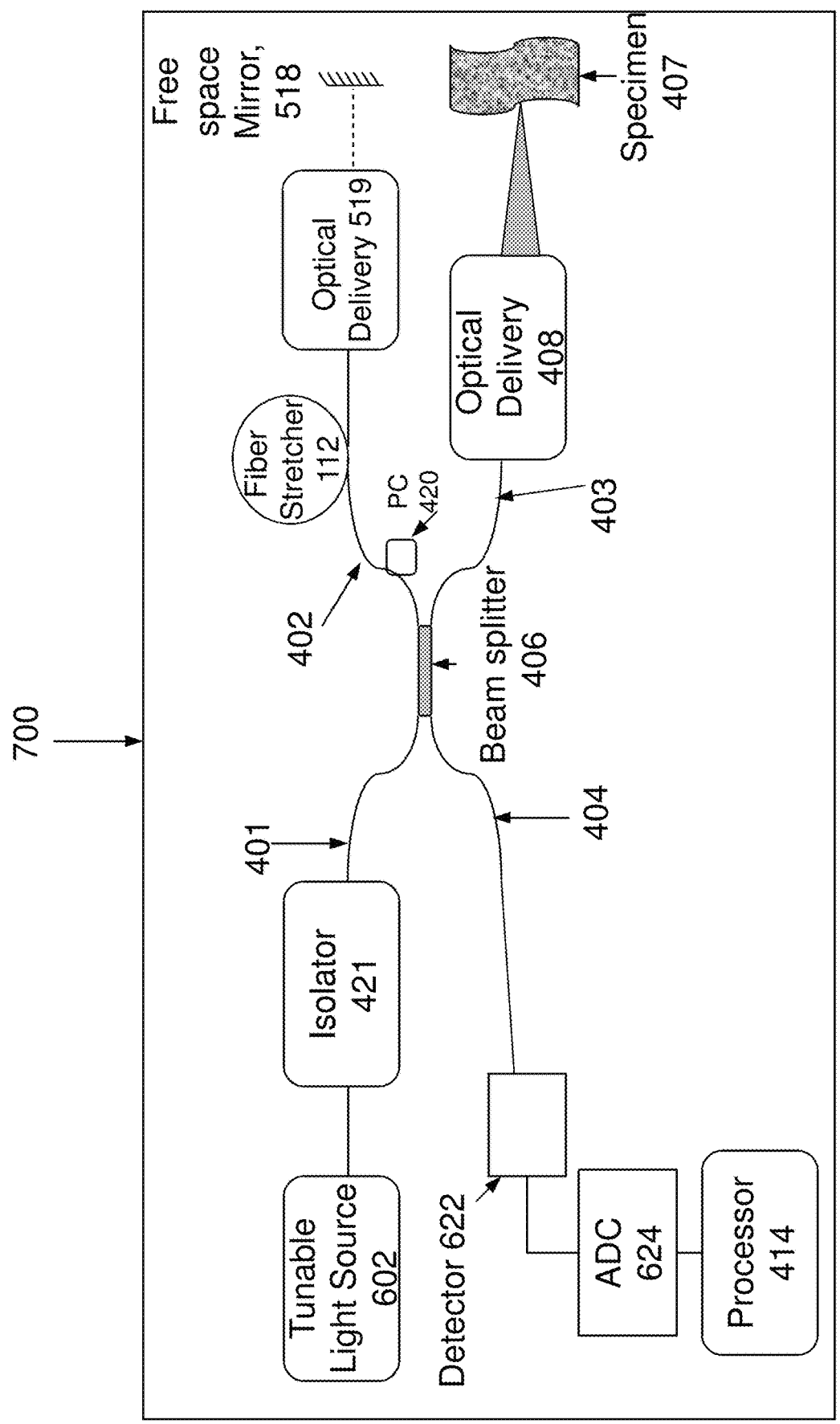
FIG. 7 is a block diagram of the OFDR-OCT system 700 similar to that in FIG. 6 except that the fiber optically integrated mirror is replaced by a free space mirror. This system can be incorporated into a foldable ophthalmic system.

FIG. 7 is a block diagram of the OFDR-OCT system 700 similar to that in FIG. 6 except that the fiber optically integrated mirror is replaced by a free space mirror 518. The light can be optionally focused on the mirror using an optical delivery unit 519. The optical delivery unit 408 can be fixed to the foldable face holder in some embodiments.

Figure 8:
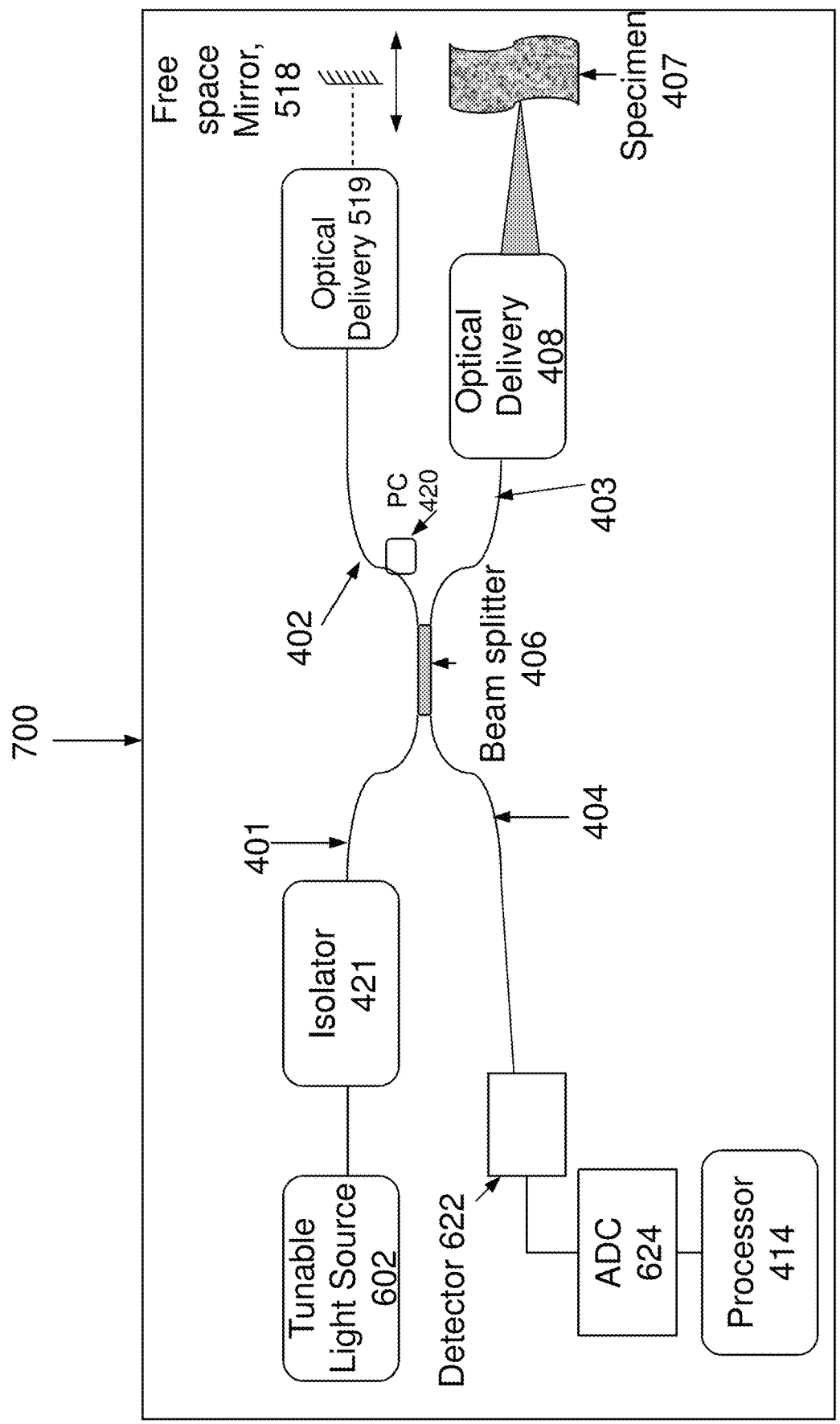
FIG. 8 is a block diagram of the OFDR-OCT system 700 without the fiber stretcher. The mirror in the reference arm is able to move back and forth. This system can be incorporated into a foldable ophthalmic system.

FIG. 8 is a block diagram of the OFDR-OCT system 700 without the fiber stretcher. The mirror 518 in the reference arm is able to move back and forth to match with the pathlength in the sample arm. The mirror motion can be achieved by a translation stage or a motorized stage or a galvanometer or a scanner. The foldable face holder comprises of the optical delivery unit 408 in some embodiments.

Extensions of the proposed interferometer: An OFDR/OCT interferometric 2D imaging system can be constructed using the proposed interferometric system where the 2D images are obtained by laterally scanning the beam incident on the sample using a 1-D scanning mirror (which is a part of the optical delivery unit). An interferometric 3D imaging system can be constructed using the proposed interferometric system where the 3D data-sets are obtained by 2D laterally scanning the beam incident on the sample using a 2-D scanning mirror (which is a part of the optical delivery unit).

Bulk of the components of the OCT/OFDR system can be placed in the base of the foldable ophthalmic system in some embodiments. The optical delivery unit in the sample arm can focus light on the eye, and can be folded as needed. The optical delivery unit can be attached to the face holder in some embodiments.

In some embodiments, the OCT/OCDR/OFDR apparatus/system operates on batteries. In some other embodiments, these batteries can be rechargeable batteries. The batteries can be charged independently or by connecting a charger to the apparatus. The charger can source power from the electrical wiring in a building. The charger (termed a vehicle charger) can also source power from a vehicle such as a car or a bus or a truck or a van. The charger can also source power from the vehicle's engine.

Method of Image Acquisition and Analysis

Figure 9:
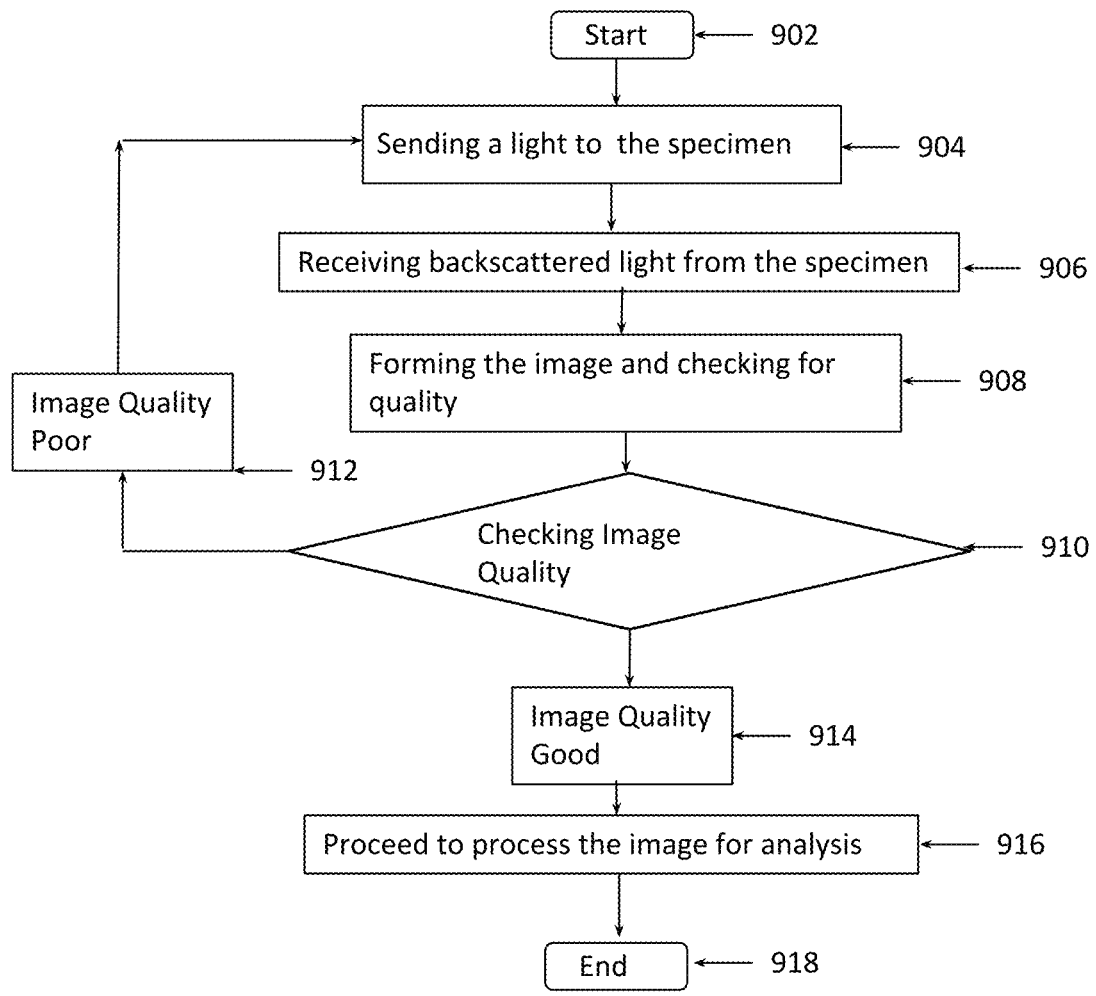
FIG. 9 is a flow chart describing a method of acquiring an image from a specimen using the OCDR-OCT system.

FIG. 9 describes a method of acquiring an image from a specimen using the OCDR-OCT sub-system. A light source may be a tunable light source, a broadband source, or a laser. An apparatus or system is used to send a specific bandwidth light from a light source to a specimen 904 using a source arm and sample arm. A backscattered light from the specimen is received 906 by the optical delivery unit. An image is formed 908 after going through the grating and detector array and checked for quality 910. If the image quality is poor 912, the steps from 904 are repeated. If the image quality is good 914 data is further sent to produce an image for analysis 916 using the processor algorithms. The process ends once the image is formed 918. The foldable face-holder comprises of the optical delivery unit 408 in the sample arm.

Figure 10:
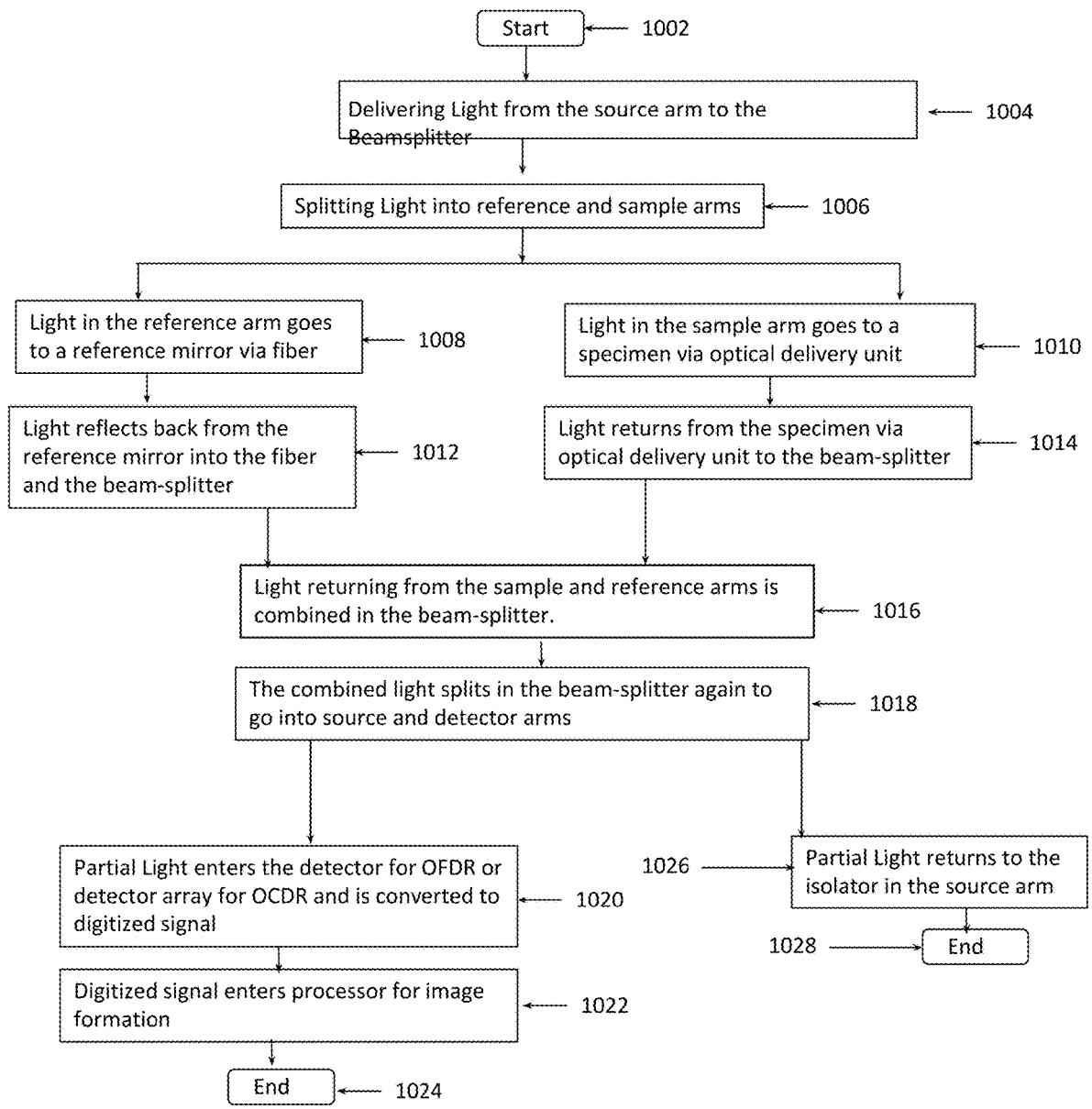
FIG. 10 is a flow chart of a method describing the usage of the apparatus.

FIG. 10 describes the steps of light travelling through the source to the specimen and the signal from the light being processed. Light is being delivered using a light source using the sample arm to the beam splitter 1004. Beam splitter splits the light into two parts sending the first path light to reference arm 1008 and second path light into the sample arm 1010. The second path light goes to the specimen via the optical delivery unit. The specimen in this case may be a human or an animal eye. Since the blood flows at irregular intervals and the picture is not static at times; stationary-object light-backscattering, moving-object-light-backscattering and combined-object-light-backscattering are returned to the beam splitter.

Sample arm sends the second path of light to the specimen (or the eye) using the optical delivery unit and the specimen (or the eye) reflects back the second path of light as a returning light via the optical delivery unit to the beam splitter 1014. A reference mirror returns the light into the fiber to be combined with the returning light from the specimen at the beam splitter 1016. Thus, the reference mirror in the reference arm returns the first path light to the beam splitter to join a returning light from the eye or the specimen. The combined light splits in the beam splitter again to go into source and detector arms 1018. A partial returning light from the beam splitter travels through a detector arm to a grating unit and a detector array in OCDR-OCT system or enters the detector if it is OFDR-OCT system to be converted to digitized signal 1020 using analog-to-digital-converter 624. Digitized signal enters the processor for A-scan generation and/or image (B-scans) formation 1022. The method ends there 1024. On the other hand partial light returns to the isolator using the source arm 1026 and the method ends there 1028. The foldable face-holder comprises of the optical delivery unit 408 in the sample arm.

Figure 11:
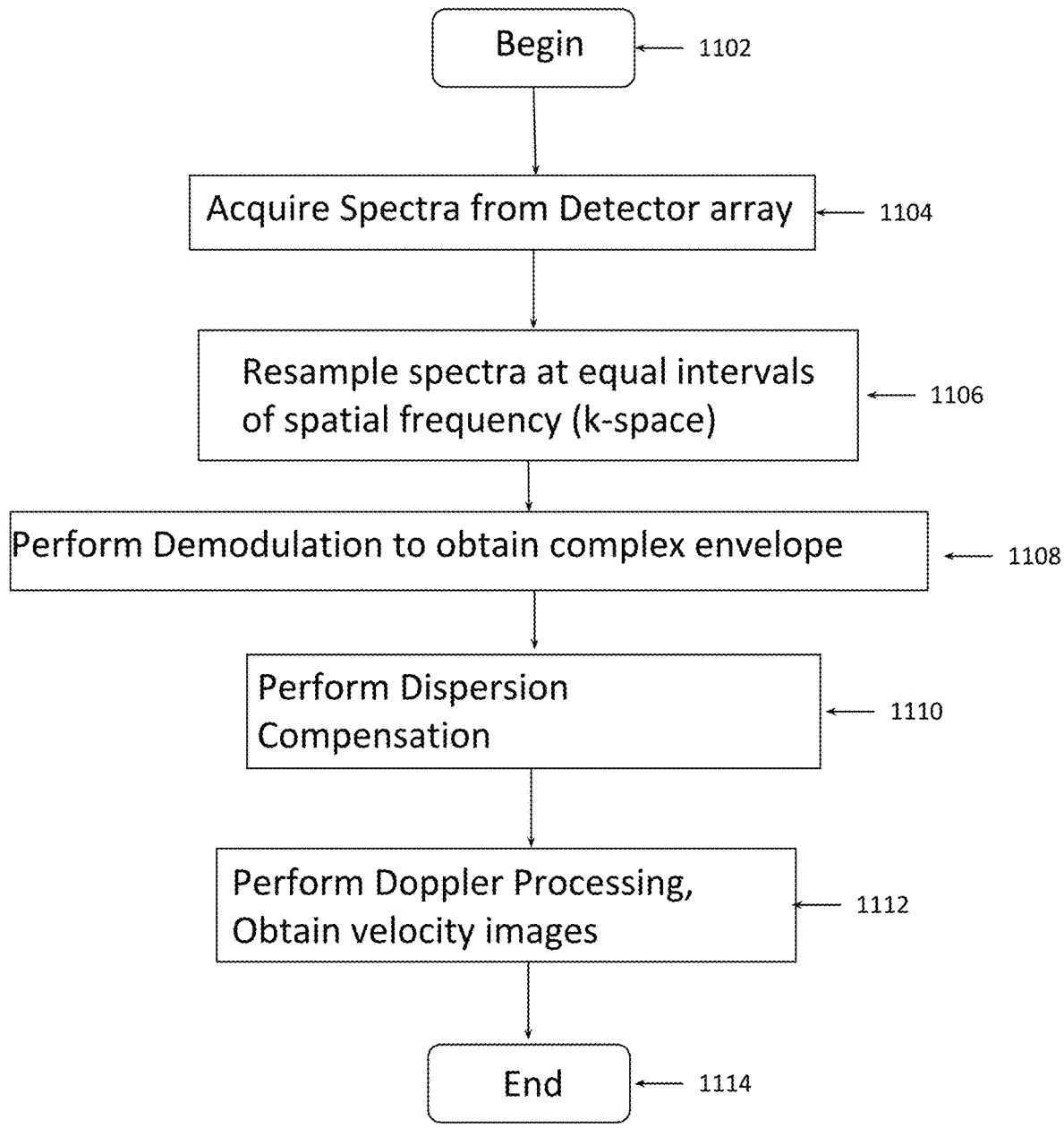
FIG. 11 is a flow chart of methods of the signals and images being processed from the start to finish.

FIG. 11 shows a high level flow of the processing algorithms. Step 1102 is the beginning step. For the OCDR-OCT system, the spectra are acquired from the detector array as explained earlier (Step 1104). Since the acquired spectra are typically spaced in equal intervals of wavelength, in the step 1106, the spectra are resampled at equal intervals of spatial frequency (k-space) using a frequency resampling algorithm. Next in step 1108, demodulation, which includes inverse Fourier transforming, is performed to extract the complex envelope of the signal. Next in order to correct for the dispersion in the system, the dispersion compensation is performed in step 1110. Next in step 1112, Doppler processing is performed to extract velocity images. The method ends in step 1114. These algorithms are processed in a processor 114 and displayed as a gray scale or pseudo-color image. By way of example, not by limitation, this processor can be a computer, Field Programmable Gate Array (FPGA), an embedded system or a microcontroller.

Frequency Resampling: The spectra $W_{ccd}(\lambda,x)$ measured by the spectrometer (i.e., the output of the digital array) are equally spaced in wavelength ($\lambda$). However in order to obtain an accurate A-scan measurement by inverse Fourier transforming, the spectra need to be re-measured at equal intervals of spatial frequency ($k=1/\lambda$). Thus, if N is the total number of samples, the spectra are measured at equal intervals in wavelength $\delta\lambda=(\lambda\ max-\lambda\ min)/N$. The spectra need to be equally spaced in k-space. Thus, if the corresponding maximum and minimum wavenumbers are k max=1/$\lambda$ min and k min=1/k max, then the spectra need to be re-sampled at equal intervals in k given by $\delta k=(k\ max-k\ min)/N$ to obtain $S_{ccd}(k,x)$. If the data are over-sampled while re-sampling by a factor of X, then $\delta k=(k\ max-k\ min)/XN$.

There are many algorithms for re-sampling the spectra. One such method is simple linear interpolation as described by [Vergnole et al 2010]. Thus, if we need to calculate the spectrum $S_{ccd}(k_0,x)$ at a location $k_0$, and the spectra are measured at the nearest neighboring wavenumbers $k_u$ (upper wavenumber=1/$\lambda_u$, $\lambda_u$ is the upper wavelength), $k_l$ (lower wavenumber=1/$\lambda_l$, $\lambda_l$ is the lower wavelength)

$$\text{Then } S_{ccd}(k_0) = S_{ccd}(k_l) + U_0[S_{ccd}(k_u) - S_{ccd}(k_l)]; \ U_0 = \frac{k_0 - k_l}{k_u - k_l}$$

and note that $S_{ccd}(k_l)=W_{ccd}(\lambda_l,x)=$ and $S_{ccd}(k_u)=W_{ccd}(\lambda_u,x)$ Another method described by [Vergnole et al. 2010] is spline interpolation. A preferred and faster method of interpolation is achieved by convolution using a Kaiser-Bessel window as described by [Vergnole et al. 2010]. $S_{ccd}(k_0)=\Sigma_{l=-M/2}^{M/2} S_{ccd}(k_l)C_0(k_l)$ where $k_l$ are the non-linearly placed neighboring values of wavenumbers, M is the size of the convolution kernel. M can be any value, however a value between 3 to 9 can yield good results.

$$C_0(k_l) = \frac{I_0\left(\gamma\sqrt{1-\left(\frac{2H}{M}\right)^2}\right)}{M}$$

where H=smaller of $$\frac{M}{2}$$

or $(k-k_l)/\delta k$ and $I_0$ is the zero-order Bessel function of the first kind. To the best of our knowledge, this is the first time a convolution based interpolation method is used for the OCDR/OFDR/OCT sub-system, which can be either folded in a suit-case/brief-case or its optical delivery unit in the sample arm can be folded.

Figure 12:
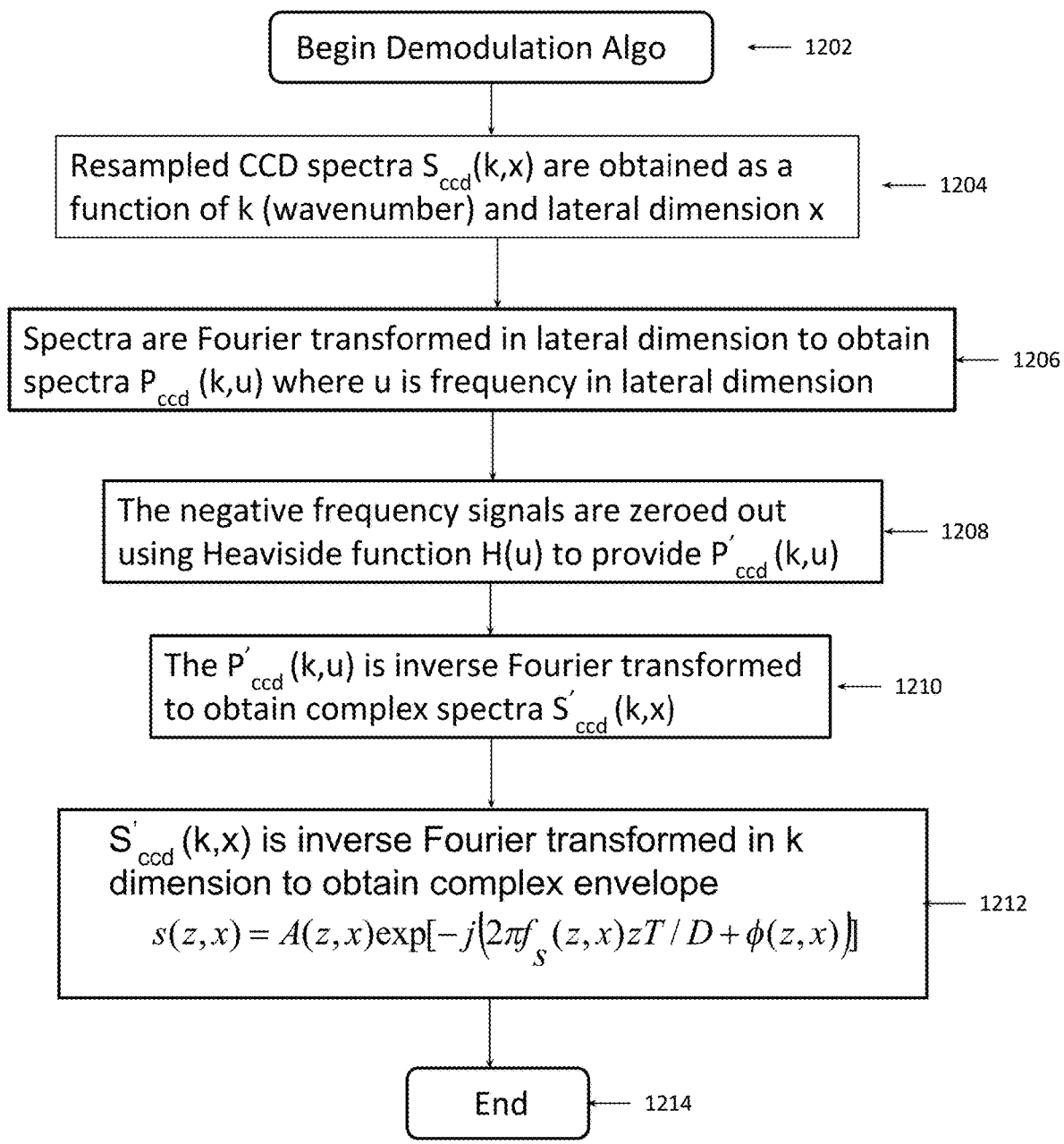
FIG. 12 is a flow chart of a method of demodulating the signal to recover the complex envelope of the OCT/OCDR/OFDR signal.

Next in FIG. 12, we present a novel algorithm such as a demodulation algorithm (step 1202), which is also instant version of the modified Hilbert transform algorithm:

1) Resampled CCD spectra $S_{ccd}(k,x)$ are obtained as a function of k (wavenumber) and lateral dimension x (step 1204).
2) Spectra are Fourier transformed in lateral dimension to obtain spectra $P_{ccd}(k,u)$ where u is frequency in lateral dimension (step 1206).
3) The negative frequency signals are zeroed out using Heaviside function H(u) to provide $P'_{ccd}(k,u)$ (step 1208).
4) The $P'_{ccd}(k,u)$ is inverse Fourier transformed to obtain complex spectra $S'_{ccd}(k,x)$ (step 1210).
5) $S'_{ccd}(k,x)$ is inverse Fourier transformed in k (i.e., depth) dimension to obtain complex envelop in Eq. 2 (step 1212)

$$s(z,x)=A(z,x)\exp[-j(2\pi f_s(z,x)zT/D+\phi(z,x))]. \quad (Eq. 6)$$

Here A(z,x) is the amplitude of the detected signal corresponding to the depth-resolved reflectivity obtained in conventional OCT imaging and $\phi(z,x)$ is the phase corresponding coherent interference of backscattered waves, commonly known as speckle. Here z is the depth location, x is the lateral location, D is total depth of A-scan, T is the time taken to acquire an A-scan. For a broadband source, A(z,x) is a highly localized function (e.g., a Gaussian) whose width determines the axial resolution of the OCT image. $f_s$ is Doppler shift in light backscattered from moving objects in the sample. A scatterer in the sample moving with a velocity $V_s$ induces a Doppler shift in the sample arm light by the frequency $$f_s=2V_s[\cos\theta]n_t v_0/c \quad (Eq. 7)$$

where $\theta$ is the angle between the sample probe beam and the direction of motion of the scatterer, $n_t$ is the local tissue refractive index, $v_0$ is the source center frequency, and c is the light velocity.

Dispersion compensation: Group velocity dispersion needs to be matched between the reference and sample arms. In some embodiments of the instant invention, dispersion is compensated numerically by flattening the Fourier domain phase of a mirror reflection. Current proposed procedure comprises of:
a) Measuring the interferogram by placing a mirror in the sample, computing the complex envelope $m_s(z)=A_m(z)\exp(j\varphi_m(z))$ [Here z is distance in depth, $A_m$ is amplitude and $\varphi_m$ is phase) for the interferogram. Such an intrerferogram can also be measured by removing the sample/specimen in the sample arm.
b) Computing the complex envelope for each interferogram measurement for any desired specimen as described in FIG. 12.
c) Multiplying the complex envelope by $\exp(-j\varphi_m(z))$ to perform dispersion compensation.

Coherent Deconvolution or complex deconvolution for Dispersion Compensation: Another process known as coherent deconvolution. The coherent deconvolution process comprises of
a) Measuring the interferogram by placing a mirror in the sample, computing the complex envelope $m_s(z)=A_m(z)\exp(j\varphi_m(z))$ (Here z is distance in depth, $A_m$ is amplitude and $\varphi_m$ is phase) for the interferogram. S such an intrerferogram can also be measured by removing the sample/specimen in the sample arm.
b) Computing the Fourier transform of $m_s(z)$ to obtain $M_s(k)$, where k is spatial frequency,
c) Computing the complex envelope s(z,x) for each interferogram measurement for any desired specimen,
d) Computing the Fourier transform of s(z,x) to obtain S(k,x),
e) Dividing S(k,x) by $M_s(k)$ to obtain $S_1(k,x)$,
f) Multiplying $S_1(k,x)$ by a Wiener filter to obtain $S_2(k,x)$ and
g) Computing inverse Fourier transform to obtain dispersion corrected sample measurement $s_2(z, x)$.

Figure 13:
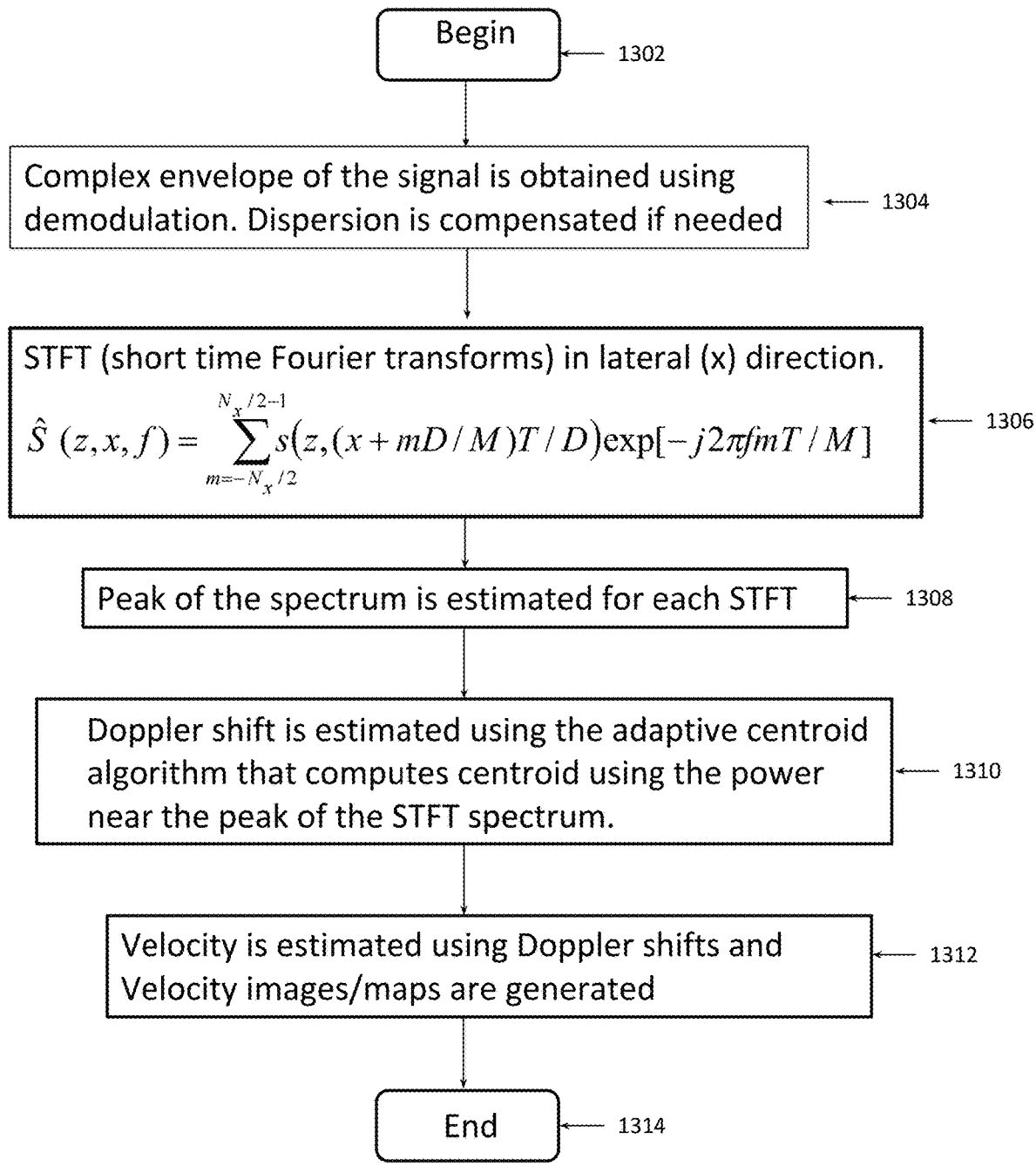
FIG. 13 is a flow chart of a method of Doppler processing the signal to estimate the Doppler shift and the corresponding velocities of the particles in the specimen.

In FIG. 13, Doppler processing algorithm for high accuracy and high precision velocity estimation is described (step 1302). The data set resulting from the camera can be processed in the processor 414 by the proposed Doppler algorithm which computes STFT (short time Fourier transforms) in lateral (x) direction (step 1306).

$$\hat{S}(z, x, f) = \sum_{m=-N_x/2}^{N_x/2-1} s(z, (x+m)T)\exp[-j2\pi fmT] \quad (Eq\ 8)$$

where $N_x$ is the number of A-scans in the STFT window. Next the peak of the STFT spectrum is estimated (step 1308). Next, the Doppler shift is computed by an adaptive centroid algorithm (which computes centroid using the power near the peak of the STFT spectrum) (step 1310). Next, the velocity is estimated using Doppler shifts and Velocity images/maps are generated (step 1312). Step 1314 is the end of Doppler processing. The velocity precision is given by $$V_s^{up}=c/(2N_xTv_0 n_t \cos\theta) \quad (Eq\ 9)$$

Doppler shift algorithm is used for estimating Doppler shifts by computing the centroid of the short time Fourier transform spectrum using power near the spectral peak, which is an adaptive centroid algorithm. As we can see, velocity precision is higher with higher T (A-scan acquisition period). Therefore, in order to detect micro-flow (~100 to 800 microns/s speed) in capillaries, by way of example but not by limitation, we can choose an A-scan rate of e.g., 2560 A scans/s. The maximum retinal blood flow velocities typically range to 1-4 cm/s. By way of example but not by limitation, higher velocities can be measured by performing another scan at a much higher speed of 42000 A scans/s. By way of example but not by limitation, from Eq. 4, choosing $N_x$ between 1 to 30, we can measure velocities as low as 15 mm/s to 0.5 mm/s, respectively. By way of example but not by limitation, we can scan retina at 2 different scan rates, viz., 2560 A scans/s and 42000 A scans/s. By way of example but not by limitation, in the first set, we can scan 10 concentric circles centered at the optic disc, each comprising of 100 A-scans, which can be acquired in 4 seconds. By way of example but not by limitation, the second set would be acquired at the same locations, 10 concentric circles, each consisting of 420 A-scans, which can be acquired in 1 s. The scanning may be performed by the disc of the retina by performing concentric circles at a variety of speed. Optical delivery unit in the sample arm creates scan patterns, wherein the scan-pattern comprises of at least two B-scans, each B-scan having its specific A-scan rate.

Thus, we propose scan-patterns comprising of at least two B-scans wherein the first B-scan's A-scan rate is slower than the A-scan rate in the second B-scan.

In an embodiment, the scan-pattern can comprise of at least two B-scans, each B-scan having its specific A-scan rate.

This Doppler processing step can used to estimate blood flow velocities for augmenting diagnosis of diabetic retinopathy. By acquiring B-scans at various locations, this can be used to obtain a 3-dimensional map of blood flow velocities or blood vessels in the retina as well as any organ of a human or animal body.

The method of FIG. 11 is also applicable for an OFDR-OCT system. In the OFDR-OCT system, the light entering the detector arm from the beam splitter is incident on the detector and converts to an interferometric electric current or signal. The tunable light source produces a light of various frequencies within a specific bandwidth. This frequency/wavelength sweeping is performed at a very high speed and the detector is able to measure the interference signal at each of the frequencies. Such a high speed measurement produces a spectrum for further processing (step 1104 in FIG. 11). These spectra are typically measured at equal intervals of wavelength. Therefore, the spectra measured by the detector are processed using a re-sampling algorithm. Thus, the spectra are resampled at equal intervals of spatial frequency (k-space) (step 1106). There are some specialized OFDR-OCT systems where the source is able to sweep the bandwidth at equal intervals of spatial frequency (k-space). In those cases, the resampling algorithm is not needed. Next the signal is demodulated to extract its complex envelope (step 1108) and generate A-scans. The absolute part of the complex envelope (A-scan) is traditional OFDR-OCT signal. Next, the dispersion compensation is performed so that the signal has better depth resolution and higher fidelity (step 1110). Finally, Doppler processing is performed to obtain velocity images, which has velocity information within various locations within a specimen (or an eye) (step 1112).

Foldable System Description

OCDR-OCT system 400 and OFDR-OCT 600 are able to image sub-surface retinal microstructure and has been useful for diagnosis and management of diabetic retinopathy.

In some other embodiments, the foldable face-holder system is used for optical coherence tomography (OCT) imaging and the OCT system comprises of a depth-scanning reference mirror to implement time-domain OCT (as described in Huang et al 1991, Fercher 1996, U.S. Pat. No. 5,321,501).

In some embodiments, compact, portable OCT-OCDR systems/apparatus (as described in U.S. patent application Ser. Nos. 12/706,717, 12/732,484, 13/723,006, 12/941,991) can be used as these systems/apparatus can easily fit in a box or a briefcase.

Various materials can be used to construct the foldable face-holder apparatus/system. Some examples are (not by limitation) 6061 aluminum alloy (i.e., UNS A96061) and its various varieties including (but not limited to) 6061-O, 6061-T4, 6061-T4 etc.; Nickel-chromium alloys such as INCONEL® (a registered trademark of the INCO family of companies) alloy 600; stainless steel and related alloys (e.g., UNS N02200, UNS N02201, UNS N04400, UNS N06600, UNS N06625, UNS N08800, UNS N08825, UNS N10276, UNS N08020, etc.) heat and chemical resistant polymers such as TOPAS® COC (by Topas Advanced Polymers). Acetal homopolymer such as Dupont's Delrin® can also be used as these polymers are tough, can sustain high stress and strain and are strong, and yet easily moldable.

Some more materials that can be used to construct the foldable face-holder apparatus or system include (not by limitation) High-density polyethylene (HDPE), Polyvinyl chloride (PVC), Acrylonitrile butadiene styrene (ABS), Polyether ether ketone (PEEK).

The apparatus or system can be built (by way of example and not by limitation) by the process of reaction injection molding, which can produce high-strength, lightweight and flexible parts using thermosetting polymers such as polyurethane.

The apparatus or system could also be built (by way of example and not by limitation) by structural reaction injection molding (SRIM), where fiber meshes are used as a reinforcing agent.

The apparatus or system could also be built (by way of example and not by limitation) by injection molding, using thermoplastics or thermosetting plastics.

The apparatus or system could also be built (by way of example and not by limitation) by normal machining and assembly.

In some embodiments, the chin-rest and/or the face-holder can slide in and out from the side of the ophthalmic system's base. In some embodiments the base comprises of OCT/OCDR/OFDR components.

In some embodiments, the chin-rest and/or the face-holder can be folded completely and slides in the instruments' system's side. In some embodiments the base comprises of OCT/OCDR/OFDR components.

In some embodiments, the ophthalmic system comprises of at least one means to hold the face of a patient (i.e., face-holder), an ocular diagnostic or therapeutic component and the means to remove the face-holder 112 from the apparatus/system and attach to the patient's face. The face-holder's eye-piece 112 is attached to the eyes using a head-band.

In some other embodiments, the face-holder is attached to the eyes using spectacles-type assembly. The eye-piece may be moved from one eye to the other for analyzing both the eyes. The eye-piece may be a part of the optical delivery unit focusing light on the eye.

In some embodiments the face-holder comprises of the optical delivery unit of the sample arm of the OCT/OCDR/OFDR systems described previously.

In some embodiments, the optical delivery unit is integrated with the face-holder of the foldable ophthalmic system.

In some embodiments the eye-piece is a part of the optical delivery unit of the sample arm of the OCT/OCDR/OFDR systems described previously.

In some embodiments the spectacles type assembly facilitates the movement of the optical delivery unit of the sample arm of the OCT/OCDR/OFDR system from one eye to the other for analyzing both the eyes.

In some embodiments, the spectacles type assembly facilitates the movement of the eye-piece of at least one of the fundus photography system, scanning retinal imaging system, perimeter, corneal topographer, auto-refractors, and many other ophthalmic modalities from one eye to the other for analyzing both the eyes.

The foldable face-holder apparatus/system and related systems could comprise of fundus photography (http://en.wikipedia.org/wiki/Fundus_photography), scanning retinal imaging (e.g., T R Friberg, A Pandya et al 2003), perimetry, corneal topography, auto-refractors, and many other ophthalmic modalities.

INDUSTRIAL APPLICATIONS

OCDR-OCT system and apparatus of this instant application is very useful for diagnosis and management of ophthalmic diseases such as retinal diseases and glaucoma etc. Instant innovative OCDR-OCT diagnostic system leverages advancements in cross technological platforms. This enables us to supply the global market a low-cost, portable, robust OCDR-OCT imaging tool, which would be affordable to general physicians, optometrists and other health personnel.

The ophthalmic system and apparatus of this instant application is very useful for diagnosis and management of ophthalmic diseases such as retinal diseases and glaucoma etc. Instant innovative ophthalmic diagnostic system leverages advancements in cross technological platforms. This enables us to supply the global market a low-cost, portable, robust ophthalmic tool, which would be affordable to general physicians, optometrists and other health personnel.

It is to be understood that the embodiments described herein can be implemented in hardware, software or a combination thereof. For a hardware implementation, the embodiments (or modules thereof) can be implemented within one or more application specific integrated circuits (ASICs), mixed signal circuits, digital signal processors (DSPs), digital signal processing devices (DSPDs), programmable logic devices (PLDs), field programmable gate arrays (FPGAs), processors, graphical processing units (GPU), controllers, micro-controllers, microprocessors and/or other electronic units designed to perform the functions described herein, or a combination thereof.

For a mechanical hardware implementation, the embodiments (or modules thereof) can be implemented using various fabrication or prototyping methods.

When the embodiments (or partial embodiments) are implemented in software, firmware, middleware or microcode, program code or code segments, they can be stored in a machine-readable medium (or a computer-readable medium), such as a storage component. A code segment can represent a procedure, a function, a subprogram, a program, a routine, a subroutine, a module, a software package, a class, or any combination of instructions, data structures, or program statements. A code segment can be coupled to another code segment or a hardware circuit by passing and/or receiving information, data, arguments, parameters, or memory contents.

What is claimed is:

1. An ophthalmic system comprising of
at least one means to hold the face of a patient called a face-holder;
wherein the face-holder can be folded at least once; and
the face-holder further comprises of a forehead rest, which is a resting pad to rest the forehead;
a light source emitting light of a specific bandwidth called a first light;
the light source operates at a center wavelength λ;
a beam splitter to split the first light from a source arm to a reference arm and a sample arm;
the sample arm further comprising of an optical delivery unit;
the optical delivery unit is further integrated with the face-holder;
the sample arm sends the second path of light to an eye using the optical delivery unit and the eye reflects back the second path of light as a returning light via the optical delivery unit to the beam splitter;
a reference mirror in the reference arm returning the first path light to the beam splitter to join a returning light from the eye;
a partial returning light from the beam splitter travels through a detector arm to a grating unit;
the grating unit disperses the partial returning light from the beam splitter and a dispersed light enters the detector array to produce a light spectrum; and
a processor performs a data analysis using a specific algorithm on the light spectrum;
and the processor generates A-scans of the eye;
a base; and
the system fits in at least one of a box, a tablet and a briefcase;
and the system comprises of at least one of ophthalmic imaging, perimetry, corneal topography, auto-refractors, fundus photography, scanning retinal imaging, and a therapeutic component.

2. The system of claim 1; further comprising of at least one part made using at least one of High-density polyethylene, Polyvinyl chloride, Acrylonitrile butadiene styrene, Polyether ether ketone, 6061 aluminum alloy, various varieties of 6061 aluminum alloy, Nickel-chromium alloys, stainless steel, stainless steel related alloys, heat and chemical resistant polymers, and Acetal homopolymer.

3. The system of claim 1; where at least one part of the system is built using at least one of machining, structural reaction injection molding, reaction injection molding, injection molding, thermoplastics and thermosetting plastics.

4. The system of claim 1; wherein the specific algorithm further comprises of at least one of frequency resampling, demodulation, dispersion compensation, and Doppler processing algorithms.

5. The system of claim 4; wherein
the frequency resampling comprises of at least one of linear interpolation, spline interpolation, convolution using a Kaiser-Bessel window;
the demodulation algorithm comprises of a modified Hilbert transform where the light spectra are Fourier transformed in a lateral direction;
the dispersion compensation comprises of at least one of coherent deconvolution and flattening the Fourier domain phase of a mirror reflection;
the Doppler processing algorithm comprises at least one of short time Fourier transforms, computing a centroid of the short time Fourier transform; an adaptive centroid algorithm.

6. The system of claim 1; further comprising of at least one feature selected from the following group:
the face-holder can be ejected from the base;
the face-holder can be folded by collapsing multi-stage telescopic legs;
the face-holder comprises of a chin-rest and a forehead rest and only the portion between the chin-rest and the base is collapsible using the multi-stage telescopic legs;
a folding hinge near the chin-rest;
a folding hinge for the face holder near the instrument base;
the chin-rest can be removed using a button from the base;
the chin-rest is attached to the base;
the chin-rest is attached to a pole of the face-holder;

the chin-rest can be removed from the pole of the face-holder;
a projector to display;
at least one of a touch-sensitive display screen, and a display having stereoscopic capabilities;
the system operates on at least one of batteries and rechargeable batteries;
a vehicle charger to charge the batteries by sourcing power from a vehicle;
at least one waveplate;
an eye-fixation target;
the optical delivery unit comprises of at least one of galvanometer and a MEMS mirror;
the processor generates B-scans using A-scans and the optical delivery unit generates scan-patterns comprising of at least two B-scans, each B-scan having its specific A-scan rate;
the eye-piece has railings to move it forward and backward with respect to the patient's eye;
the chin-rest and the face-holder can be folded completely and slides in the system's side.

7. The system of claim 6; where at least one waveplate is a $(2M+1)\lambda/m$ waveplate where M and m are integers.

8. The system of claim 7; where the waveplate is created using an optical fiber.

9. An ophthalmic system comprising of
at least one means to hold the face of a patient called a face-holder;
a face holder comprising of a spectacles-type assembly attached to the eyes; and
a tunable light source;
the tunable light source produces a light of various frequencies within a specific bandwidth;
a beam splitter to split the first light from a source arm to a reference arm and a sample arm;
the sample arm further comprising of an optical delivery unit;
the sample arm sends the second path of light to an eye using the optical delivery unit and the eye reflects back the second path of light as a returning light via the optical delivery unit to the beam splitter;
a reference mirror in the reference arm returning the first path light to the beam splitter to join a returning light from the eye;
a partial returning light from the beam splitter travels through a detector arm to a detector;
the detector further directs the signal to an analog to digital converter to generate a digitized signal; and
the digitized signal is directed towards a processor; and such a measurement produces spectra;
the processor analyzes the digitized signal using a specific algorithm;
and the processor generates A-scans of the eye;
at least one of a projector to display and a display screen;
a base; and
the system fits in at least one of a box, a tablet and a briefcase.

10. The system of claim 9; wherein the specific algorithm further comprises of at least one of frequency resampling, demodulation, dispersion compensation, and Doppler processing algorithms.

11. The system of claim 10; wherein
the frequency resampling comprises of at least one of linear interpolation, spline interpolation, convolution using a Kaiser-Bessel window;
the demodulation algorithm comprises of a modified Hilbert transform where spectra are Fourier transformed in a lateral direction;
the dispersion compensation comprises of at least one of coherent deconvolution and flattening the Fourier domain phase of a mirror reflection;
the Doppler processing algorithm comprises at least one of short time Fourier transforms, computing a centroid of the short time Fourier transform; an adaptive centroid algorithm.

12. The system of claim 9; where the processor is selected from a group consisting of a computer, an integrated circuit, an application specific integrated circuit, a field programmable gate array, a graphical processing unit, an embedded system and a microcontroller.

13. The system of claim 9 further comprising of at least one feature selected from the following group:
an eye-piece in the spectacles-type assembly may be moved from one eye to the other for analyzing both the eyes;
the face-holder can be ejected from the base;
the display screen is at least one of a touch-sensitive screen, and a display having stereoscopic capabilities;
the system operates on at least one of batteries and rechargeable batteries;
a vehicle charger to charge the batteries by sourcing power from a vehicle;
an eye-fixation target;
the optical delivery unit comprises of at least one of galvanometer and a MEMS mirror.

14. The system of claim 9, where in at least one of the tunable light source, the processor, the reference arm, the sample arm, the detection arm, the beam splitter, the detector reside in the base.

15. An ophthalmic system comprising of at least one means to hold the face of a patient called a face-holder; wherein the face-holder can be folded at least once; and a base; and at least one of ophthalmic imaging, perimetry, corneal topography, auto-refractors, fundus photography, scanning retinal imaging, optical coherence tomography and a therapeutic component; and
further comprising of at least one feature selected from the following:
the system fits in at least one of a box, a tablet and a briefcase; a face holder comprising of a spectacles-type assembly attached to the eyes;
an eye-piece in the spectacles-type assembly may be moved from one eye to the other for analyzing both the eyes;
wherein at least one part of the system is built using at least one of machining, structural reaction injection molding, reaction injection molding, injection molding, thermoplastics and thermosetting plastics.

16. The system of claim 15; further comprising of at least one feature selected from the following group: a base;
the face-holder can be ejected from the base;
the face-holder can be folded by collapsing multi-stage telescopic legs;
the face-holder comprises of a chin-rest and a forehead rest and only the portion between the chin-rest and the base is collapsible using the multi-stage telescopic legs;
there is a folding hinge near the chin-rest;
there is a folding hinge for the face holder near the instrument base;
the chin-rest can be removed using a button from the base;
the chin-rest is attached to the base;
the chin-rest is attached to a pole of the face-holder;

the chin-rest can be removed from the pole of the face-holder;

an eye-fixation target;

the system operates on at least one of batteries and rechargeable batteries;

a vehicle charger to charge the batteries by sourcing power from a vehicle;

a projector to display;

at least one of a touch-sensitive screen and a display having stereoscopic capabilities;

the face-holder further comprises of a forehead rest, which is a resting pad to rest the forehead.

17. The system of claim 15 further comprising of at least one part made using a material selected from a group consisting of High-density polyethylene, Polyvinyl chloride, Acrylonitrile butadiene styrene, Polyether ether ketone, 6061 aluminum alloy, various varieties of 6061 aluminum alloy, Nickel-chromium alloys, stainless steel, stainless steel related alloys, heat and chemical resistant polymers, and Acetal homopolymer.

18. The system of claim 15 further comprising of at least one of evaluation and treatment of an organ selected from a group consisting of a retina, a posterior segment, a cornea, and an anterior segment.

\* \* \* \* \*